(12) United States Patent
Szita et al.

(10) Patent No.: US 12,714,995 B2
(45) Date of Patent: Aug. 25, 2026

(54) MICROFLUIDIC DEVICE

(71) Applicant: UCL BUSINESS PLC, London (GB)

(72) Inventors: Nicolas Szita, London (GB); Marcel Reichen, London (GB)

( * ) Notice: Subject to any disclaimer, the term of this patent is extended or adjusted under 35 U.S.C. 154(b) by 1404 days.

(21) Appl. No.: 17/245,070

(22) Filed: Apr. 30, 2021

(65) Prior Publication Data

US 2021/0252509 A1 Aug. 19, 2021

Related U.S. Application Data

(63) Continuation-in-part of application No. 14/705,309, filed on May 6, 2015, now Pat. No. 11,033,897, (Continued)

(30) Foreign Application Priority Data

Nov. 26, 2008 (GB) ..................................... 0821636

(51) Int. Cl.
*C12M 1/32* (2006.01)
*B01L 3/00* (2006.01)
(Continued)

(52) U.S. Cl.
CPC ....... *B01L 3/502715* (2013.01); *C12M 23/16* (2013.01); *C12M 23/26* (2013.01); *C12M 29/10* (2013.01); *B01L 2200/025* (2013.01); *B01L 2200/027* (2013.01); *B01L 2200/0689* (2013.01); *B01L 2300/0627* (2013.01); *B01L 2300/0816* (2013.01); *B01L 2300/0874* (2013.01); *B01L 2300/10* (2013.01);
(Continued)

(58) Field of Classification Search
CPC .............................. C12M 23/12; C12M 23/16
See application file for complete search history.

(56) References Cited

U.S. PATENT DOCUMENTS 6,193,647 B1 2/2001 Beebe
6,209,028 B1 3/2001 Walker et al.
(Continued)

FOREIGN PATENT DOCUMENTS

EP 1880765 1/2008
JP 2003-227780 8/2003
(Continued)

*Primary Examiner* — Jonathan M Hurst
(74) *Attorney, Agent, or Firm* — Miles & Stockbridge P.C.; Ajay A. Jagtiani

(57) ABSTRACT

A multifunctional dual mode microfluidic device including a first operating configuration and a second operating configuration wherein in the first operating configuration, the device is configured to perform static cell seeding or produce cells. In the second operating configuration, the device is configured to perform perfusion via microfluidics of the device, and the device is configured to switch between the first operating configuration and the second operating configuration. The first operating configuration and the second operating configuration are selectively and independently accessible, wherein the first operating configuration or the second operating configuration does not alter any other configuration of the device. The device is fully operable in either one of the first operating configuration or the second operating configuration.

21 Claims, 14 Drawing Sheets

Related U.S. Application Data which is a continuation of application No. 13/116,577, filed on May 26, 2011, now abandoned, which is a continuation-in-part of application No. PCT/GB2009/002778, filed on Nov. 26, 2009.

(51) Int. Cl.
*C12M 1/00* (2006.01)
*C12M 3/06* (2006.01)

(52) U.S. Cl.
CPC ..... *B01L 2300/12* (2013.01); *B01L 2400/086* (2013.01); *Y10T 409/303752* (2015.01)

(56) References Cited

U.S. PATENT DOCUMENTS 6,319,476 B1 11/2001 Victor, Jr.
6,645,432 B1 11/2003 Anderson
2004/0077075 A1 4/2004 Jensen et al.
2005/0089993 A1 4/2005 Boccazzi et al.
2006/0154361 A1* 7/2006 Wikswo ................. C12M 23/16 435/297.5
2006/0199260 A1 9/2006 Zhang et al.
2008/0057561 A1 3/2008 Takahashi
2009/0111141 A1* 4/2009 Deutsch ................. C12M 23/12 435/307.1
2010/0009335 A1 1/2010 Joseph

FOREIGN PATENT DOCUMENTS

JP 2004-000163 1/2004
WO 01/09598 2/2001
WO 01/88087 11/2001
WO 2005023124 3/2005

* cited by examiner

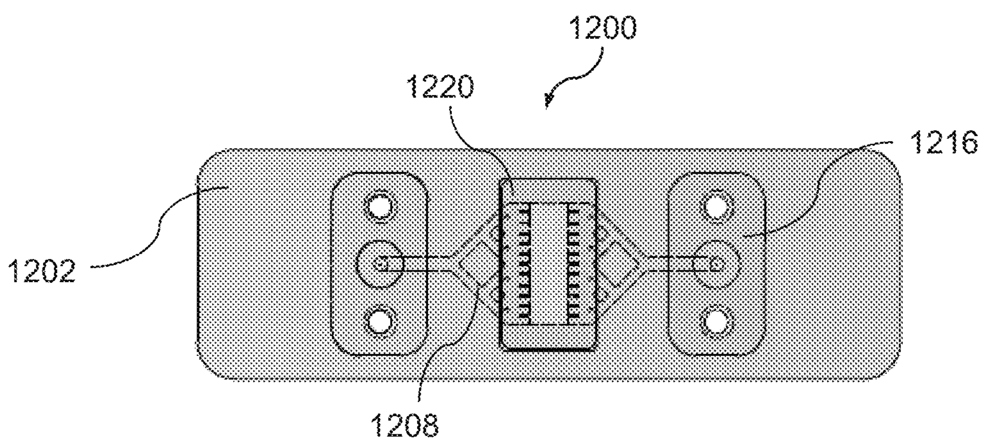
FIG. 13
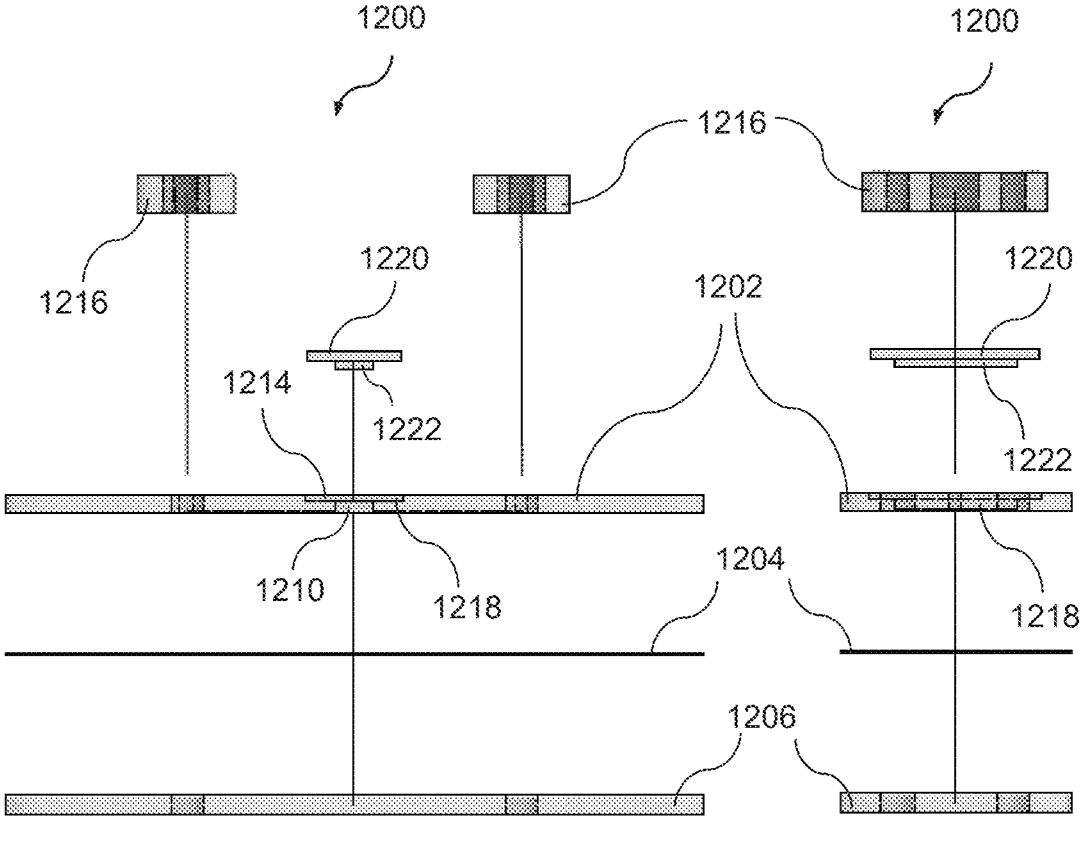
FIG. 14
FIG. 15

MICROFLUIDIC DEVICE

CROSS-REFERENCE TO RELATED APPLICATIONS

This application is a continuation-in-part application of U.S. application Ser. No. 14/705,309 filed May 6, 2015, which is a continuation of U.S. application Ser. No. 13/116,577 filed May 26, 2011, which is a continuation-in-part application of international patent application Serial No. PCT/GB2009/002778 filed Nov. 26, 2009, which published as PCT Publication No. WO/2010/061201 on Jun. 3, 2010, which claims benefit of GB patent application Serial No. 0821636.8 filed Nov. 26, 2008. The foregoing applications, and all documents cited therein or during their prosecution, together with any manufacturer's instructions, descriptions, products specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

BACKGROUND

Field of the Invention

The present disclosure relates to microfluidic devices such as bioreactors used for cell culture and for the production of cells.

Background of the Invention

Miniaturised total analysis systems ("μTAS") were proposed as a novel concept for chemical sensing in 1990 [1], creating the field of microfluidics and leading to the vision of lab-on-a-chip. μTAS integrates all steps required in chemical analysis-sampling, pre-processing, and measurement, etc.—into a single device via miniaturisation, resulting in improved selectivity and detection limit compared to conventional sensors [1]. A significant amount of research has been devoted to the development of microfluidics technology and applications of μTAS devices over the past decade [2-5]. Common analytical assays, including polymerase chain reaction (PCR) [6-9], DNA analyses and sequencing [10-13], protein separations [14-18], immunoassay [19-24], and intra- and inter-cellular analysis [25-29] have been reduced in size and fabricated in a centimetre-scale chip. The reduction in the size of the analytical processes has many advantages including rapid analysis, less sample amount, and smaller size [1-5]. The flushing of cells can also potentially lead to unwanted dissociation of cell colonies.

Although there have been many successes, an important hurdle that still needs to be cleared is the connection between the micro-components of a device and the macro-environment of the world. This part of the device is often referred to as the macro-to-micro interface [30], interconnect [31-34], or world-to-chip interface [35-39]. The difficulty results from the fact that samples and reagents are typically transferred in quantities of microlitres (μL) to millilitres (or even litres) whereas microfluidic devices consume only nanolitres (nL) or picolitres of samples/reagents due to the size of reaction chambers and channels, which typically have dimensions on the order of microns. This problem must be overcome for microfluidic devices to be successful, especially for high-throughput applications where manual manipulation is not economical and the macro-to-micro inter-face must be developed.

Microfluidic devices have also been developed for use in a broad range of cell biology applications [40]. Generally, in these devices a constant perfusion system is used to provide the cells with an adequate supply of medium in order to provide the required nutrient requirements and oxygen supply to keep the cells healthy [41]. However, the problem with using a constant perfusion or flow of medium across the cells is that the cells can be exposed to high shear stress which can be detrimental to the normal functioning of the cells. This is especially the case for highly sensitive cells such as human embryonic stem cells (hESC). Further, if high flow rates are used for the perfusion, cells may be washed out of the microfluidic device by the medium.

Another problem associated with existing microfluidic devices used in cell culture is that it is often difficult to accurately and carefully introduce cells into the culture chamber of the microfluidic device. For example, some devices flush the cells into the microfluidic chamber from upstream inlets. This leads to an undefined number of cells in the chamber. The flushing of cells can also potentially affect the phenotype of the cells as a result of exposure to high shear stress.

Citation or identification of any document in this application is not an admission that such document is available as prior art to the present disclosure.

SUMMARY

The present disclosure provides a microfluidic device comprising: a chamber having a fluid inlet, and a fluid outlet and a sealable port, wherein the fluid inlet and the fluid outlet are positioned to direct fluid flowing from the fluid inlet to the fluid outlet through the chamber, and wherein the sealable port is aligned with the chamber to allow material to be placed directly into, or removed from, the chamber from the exterior of the device when the sealable port is open, and to prevent fluid escaping through the sealable port when the sealable port is sealed, and a lid configured to seal the sealable port in a sealed position when the lid fills part of a volume of the chamber in a closed position, wherein the chamber has a smaller volume in the sealed position, wherein the lid is configured to unseal the sealable port in an unsealed position when the lid is removed from the part of a volume of the chamber in an open position, wherein the chamber has a larger volume in the open position, wherein the lid is in contact with the side walls of the chamber when the sealable port is closed, wherein the device is operable when the sealable port is open or closed, and wherein the sealable port can be opened or closed during use of the device.

In some embodiments, a method of treating cell cultures in a microfluidic device comprises: configuring the device to culture cells; culturing the cells; configuring the device to perform cell-based or enzymatic assays within the same device; and performing cell-based or enzymatic assays.

In yet another embodiment, a method of treating cells in a microfluidic device comprises: configuring the device to seed cells in the device; seeding cells in the device; configuring the device to perfuse cells in the same device; and perfusing the cells.

In some embodiments, a multifunctional dual mode microfluidic device comprises: a first operating configuration; and a second operating configuration; wherein in the first operating configuration, the device is configured to perform static cell seeding, wherein in the second operating configuration, the device is configured to perform perfusion via microfluidics of the device, and wherein the device is configured to switch between the first operating configuration and the second operating configuration.

In yet another embodiment, a multifunctional dual mode microfluidic device configured to selectively switch between two modes of operation comprises: a first operating configuration; and a second operating configuration, wherein the first operating configuration comprises an open chamber having a fluid inlet and a fluid outlet, wherein the fluid inlet and the fluid outlet are positioned to direct fluid flowing from the fluid inlet to the fluid outlet through the chamber, and wherein chamber is configured to allow material to be placed directly into, or removed from, the chamber from the exterior of the device, wherein the second operating configuration comprises a closed chamber having the fluid inlet and the fluid outlet and a sealable port, wherein the sealable port is aligned with the chamber to prevent fluid escaping through the sealable port when the sealable port is sealed, and a lid configured to seal the sealable port in a sealed position when the lid fills part of a volume of the chamber in a closed position, wherein the lid is in contact with the side walls of the chamber when the sealable port is closed, wherein the device is configured to switch between the first operating configuration and the second operating configuration, wherein the device remains operable in either the first operating configuration or the second operating configuration.

In some embodiments, a method of performing cell seeding and microfluidics in a multifunctional dual mode microfluidic device comprises: configuring the device into a first operating configuration; performing static cell seeding in the first operating configuration of the device; configuring the device into a second operating configuration; and performing perfusion via microfluidics in the second operating configuration of the device, wherein the device is configured to switch between the first operating configuration and the second operating configuration.

In yet another embodiment, a microfluidic device comprises: a chamber having a fluid inlet, and a fluid outlet; a sealable port, wherein the fluid inlet and the fluid outlet are positioned to direct fluid flowing from the fluid inlet to the fluid outlet through the chamber, and wherein the sealable port is aligned with the chamber to allow material to be placed directly into, or removed from, the chamber from the exterior of the device when the sealable port is open, and to prevent fluid escaping through the sealable port when the sealable port is sealed, wherein the chamber is formed on a first layer of the device, wherein a base of the chamber is formed from a substrate for supporting biological material, and the chamber is formed on at least a portion of the substrate, wherein the substrate is formed on another layer of the device; and a lid configured to seal the sealable port in a sealed position when the lid fills part of a volume of the chamber in a closed position, wherein the chamber has a smaller volume in the sealed position, wherein the lid is configured to unseal the sealable port in an unsealed position when the lid is removed from the part of a volume of the chamber in an open position, wherein the chamber has a larger volume in the open position, wherein the lid is in contact with the side walls of the chamber when the sealable port is closed, wherein the device is operable when the sealable port is open or closed, and wherein the sealable port can be opened or closed during use of the device.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as “comprises”, “comprised”, “comprising” and the like can have the meaning attributed to it in U.S. Patent law; e.g., they can mean “includes”, “included”, “including”, and the like; and that terms such as “consisting essentially of” and “consists essentially of” have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 7A depicts a microfluidic device with the sealable port 51 open according to one embodiment of the present disclosure.

FIG. 7B depicts a microfluidic device with the sealable port 51 closed according to one embodiment of the present disclosure. FIG. C depicts a microfluidic device with the sealable port 51 closed in which the cross section is taken perpendicular to that in FIGS. 7A and 7B according to one embodiment of the present disclosure.

FIG. 13 illustrates a top view of the microfluidic perfusion bioreactor of FIG. 12 according to one embodiment of the present disclosure.

FIG. 14 illustrates a forward side view of the microfluidic perfusion bioreactor of FIG. 12 according to one embodiment of the present disclosure.

FIG. 15 illustrates a side view of the microfluidic perfusion bioreactor of FIG. 12 according to one embodiment of the present disclosure.

DETAILED DESCRIPTION OF THE INVENTION

Definitions

Figure 1A:
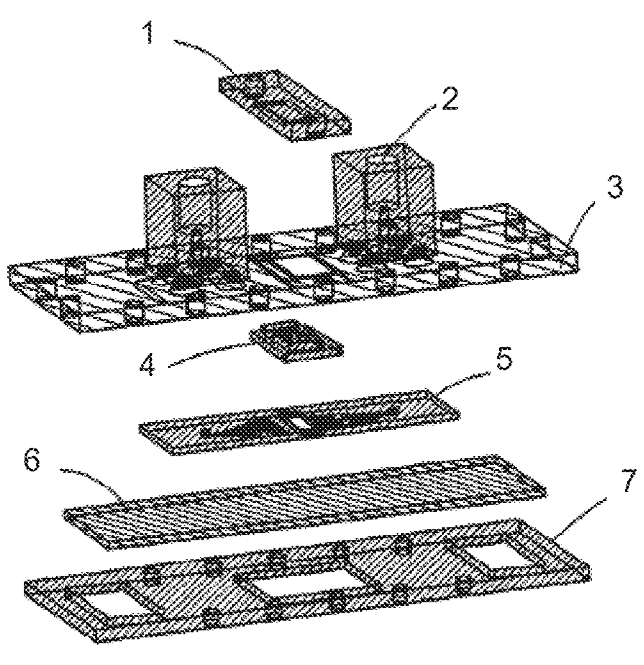
FIG. 1A depicts an exploded view of a microfluidic perfusion bioreactor (MPB) according to one embodiment of the present disclosure.

Where the definition of terms departs from the commonly used meaning of the term, applicant intends to utilize the definitions provided below, unless specifically indicated.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present disclosure, the term "comprising", the term "having", the term "including," and variations of these words are intended to be open-ended and mean that there may be additional elements other than the listed elements.

For purposes of the present disclosure, directional terms such as "top," "bottom," "upper," "lower," "above," "below," "left," "right," "horizontal," "vertical," "up," "down," etc., are used merely for convenience in describing the various embodiments of the present disclosure. The embodiments of the present disclosure may be oriented in various ways. For example, the diagrams, apparatuses, etc., shown in the drawing figures may be flipped over, rotated by 90° in any direction, reversed, etc.

For purposes of the present disclosure, a value or property is "based" on a particular value, property, the satisfaction of a condition, or other factor, if that value is derived by performing a mathematical calculation or logical decision using that value, property or other factor.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present disclosure, the term "bioreactor" refers to a device or system that supports a biologically active environment. In some embodiments, a bioreactor is a vessel in which a chemical process is carried out which involves organisms or biochemically active substances derived from such organisms. Disclosed embodiments may also refer to a device or system designed to grow cells or tissues in the context of cell culture.

For purposes of the present disclosure, the term "cell culture" refers to the process by which cells are grown under controlled conditions, generally outside their natural environment. After the cells of interest (e.g., primary cells) have been isolated from living tissue, they can subsequently be maintained under carefully controlled conditions. These conditions may vary for each cell type, but generally consist of a suitable vessel with a substrate or medium that supplies the essential nutrients (amino acids, carbohydrates, vitamins, minerals), growth factors, hormones, and gases (CO2, O2), and regulates the physio-chemical environment (pH buffer, osmotic pressure, temperature). In some instances, cells require a surface or an artificial substrate (adherent or monolayer culture) whereas others may be grown free floating in culture medium (suspension culture).

For purposes of the present disclosure, the term "cell culture device" refers to a device capable of receiving and/or processing a cell culture.

For purposes of the present disclosure, the term "culture chamber" refers to a defined area such as within an apparatus for receiving an amount of material (e.g., volume or cell number) within the disclosed device. The aforementioned material may include: cells or cell clusters, cellular grafts, or cell organoids or cell embroyids, or cell spheroids or other 3D cell constructs or indeed any 3D cell structure mimicking tissue and organs (including the required scaffolds); or small organs like adrenals, suspended or adherent cells microbial cells such as biofilms enzymes including any support structures for immobilized enzymes, such as, but not limited to, organic and inorganic supports, using any kind of reversible or irreversible enzyme immobilization method, extra-cellular matrices such as extracellular macromolecules and minerals, such as collagen, enzymes, glycoproteins and hydroxyapatite that provide structural and biochemical support to surrounding cells. In addition, any kind of proteins or gels may be applied as surface modification techniques to the chamber, such as for example the surface of the bottom chamber, to optimize operating conditions by tailoring the physical, chemical or biological characteristics of the chamber surface. The disclosed culture chamber may comprise a compartment such as within a microfluidic device comprising, for example, a three dimensional space having a floor bottom, side walls and an uppermost portion. The uppermost portion may be for the top or ceiling of the chamber and may be removable and sealable. In some embodiments, the uppermost portion of the culture chamber may be positioned at any location within the chamber thereby adjusting the volume of the chamber thereof.

For purposes of the present disclosure, the term "cell seeding" refers to spreading a defined amount (volume or cell number) of a cell suspension into or on to a surface of an apparatus such as in a flask, a culture chamber or onto a plate.

For purposes of the present disclosure, the term "culture" refers to the act or process of cultivating living material in prepared nutrient media.

For purposes of the present disclosure, the term "cyclic olefin copolymer" (COC) refers to an amorphous polymer and may be regarded as transparent amorphous thermoplastics produced by copolymerization of norbornene or docyclopentadiene with ethylene using a metallocene catalyst. These copolymers contain attractive optical properties including high clarity, high light transmissivity, low birefringence, and high refractive index. Other performance benefits include excellent biocompatibility, very low moisture absorption, good chemical resistance, excellent melt processability and flowability as well as high rigidity, elastic modulus, and strength which are retained over a wide temperature range, from about −50° C. to near their glass transition temperature.

For purposes of the present disclosure, the term "cyclo olefin polymer" (COP) refers to materials that contain, or are made from, at least one cyclic monomer. COP is resin with a wide range of high-end characteristics, including: superior moldability, low birefringence, high transparency, high heat resistance, and low water absorption. In addition, COPs may be provided as thermoplastics with high strength and rigidity.

For purposes of the present disclosure, the term "interconnect(s)" refers to the interface providing the connection between the macroscopic world (also referred to as the macro-world) and a microfluidic device (also referred to as the micro-fluidics), also known as the macro-to-micro interface. Interconnects of the disclosed embodiment enable to transport fluids in and out of the microfluidic device, for example, by connecting the microfluidic device with a connection means such as, for example, via a conduit or tubing, either reversibly or irreversibly.

For purposes of the present disclosure, the term "lid" refers to a removable or hinged cover for the top of a container. In some embodiments, a lid, also known as a cover, may be part of a container, and serve as the closure or seal, for example, one that completely closes the object. By way of example, in some disclosed embodiments, the lid may be configured to seal a sealable port structure, and, in some case, serve as a ceiling structure or top of the sealable port.

For purposes of the present disclosure, the term "parallelized/multiplexed device" refers to a device where key features are repeated a significant number of times in such a way that the same operation can be performed multiple times in parallel (i.e. in the same period of time). In one embodiment, the disclosed device may have several times the culture chamber and adjacent fluid flow channels (inlet and outlet) placed in parallel, i.e. next to each other. The different inlet channels may either be connected to one single fluid pump, centrally, or to several ones.

For our device, this means that we will have several times the culture chamber and adjacent fluid flow channels (inlet and outlet) placed in parallel, i.e. next to each other. The different inlet channels can either be connected to one single fluid pump, centrally; or to several ones.

For purposes of the present disclosure, the term "perfusion" refers to the passage of fluid or liquid through the circulatory configuration of a system. In some disclosed embodiments, passage of fluid may occur to overspread with moisture in which a fluid flow may be utilized to bring nutrients to the cells and/or remove waste product from the cells.

For purposes of the present disclosure, the term "perfusion" refers to the passage of fluid or liquid through the circulatory configuration of a system. In some disclosed embodiments, passage of fluid may occur to overspread with moisture in which a fluid flow may be utilized to bring nutrients to the cells and/or remove waste product from the cells.

For purposes of the present disclosure, the term "polydimethylsiloxane" (PDMS) (also known as also known as dimethylpolysiloxane or dimethicone) refers to a group of polymeric organosilicon compounds that are commonly referred to as silicones.

For purposes of the present disclosure, the term "polystyrene" (PS) refers to a synthetic aromatic hydrocarbon polymer made from the monomer known as styrene.

For purposes of the present disclosure, the term "microfluidic device" refers to a device which enables the culturing and processing of cells (i.e., the processing and production of cells), and generally the handling and treatment of cells to create cellular products or products from cells. Even more, disclosed embodiments may include an instrument that uses very small amounts of fluid on a microchip to do prescribed laboratory tests. Embodiments of the disclosed microfluidic device may use body fluids or solutions containing cells or cell parts to diagnose diseases. In some instances, microfluidic devices of the present disclosure may be regarded known as lab-on-a-chip.

For purposes of the present disclosure, the term "microfluidics" refers to the science of manipulating and controlling fluids in networks of channels with dimensions, for example, from tens to hundreds of micrometers. Microfluidics may refer to the behavior, precise control, and manipulation of fluids that are geometrically constrained to a small scale at which capillary penetration governs mass transport. Microfluidic systems may transport, mix, separate, or otherwise process fluids.

For purposes of the present disclosure, the term "microperfusion" refers to perfusing culture medium, such as in a microfluidic cell culture device, to utilize the fluid flow to bring nutrients to the cells and/or remove waste product from the cells.

For purposes of the present disclosure, the term "multiplexed" refers to several individual devices that may be put next to each other in a holder.

For purposes of the present disclosure, the term "parallelized" refers to a device architecture (with chamber and channels) that is replicated several times, but forms one integral device.

For purposes of the present disclosure, the term "port" refers to an opening for intake or exhaust of a fluid. In some embodiments port refers to a small opening in a container or vessel e.g., for viewing or for the controlled passage of material.

For purposes of the present disclosure, the term "sealable" refers to capability to close or make secure against access, leakage, or passage such as by a fastening or coating.

DESCRIPTION

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

Although the present disclosure and its advantages have been described in detail, it should be understood that various changes, substitutions and alterations can be made herein without departing from the spirit and scope of the invention as defined in the appended claims.

In some embodiments, a microfluidic device may include a microfluidic perfusion bioreactor and/or a microfluidic chip.

The present disclosure will now be described by way of example only with reference to the figures.

Figure 1B:
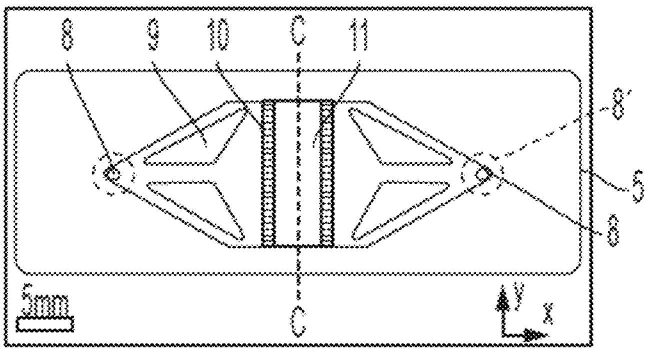
FIG. 1B is a schematic of an embodiment of a microfluidic chip depicting the channel arrangement according to one embodiment of the present disclosure.
Figure 1C:
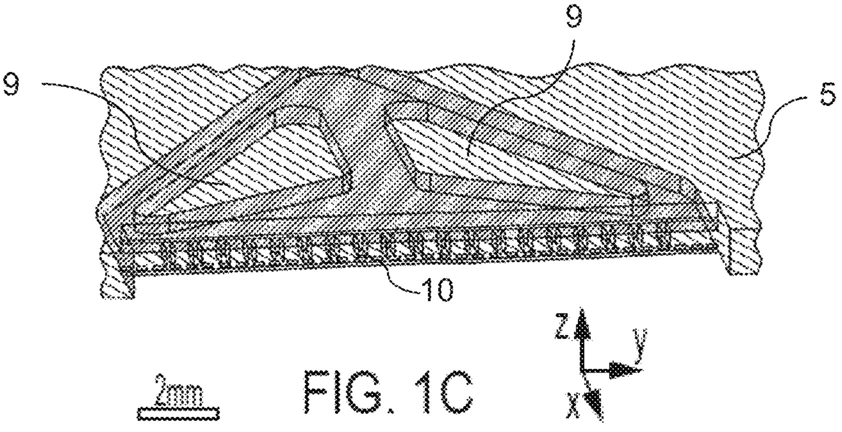
FIG. 1C is a cross-sectional perspective view along line “C” of FIG. 1B depicting a section of a microfluidic chip according to one embodiment of the present disclosure.

FIG. 1A shows solid models of a microfluidic perfusion bioreactor ("MPB"). FIGS. 1B and 1C depict a microfluidic chip 5. FIG. 1A shows an exploded view of the MPB with its components such as a lid 1, interconnects 2 for tubing, a top plate 3, a gasket 4, a microfluidic chip 5, a cell culture slide 6 and a bottom frame 7. The lid, the top plate and the bottom frame were fabricated in polycarbonate. In some embodiments, any material known in the art may be used to fabricate the lid, top plate and/or the bottom frame. The gasket and the microfluidic chip were made of PDMS. The interconnects were made of aluminum. The cell culture slide was tissue culture polystyrene. FIG. 1B shows a schematic of the channel arrangement of the microfluidic chip with an inlet/outlet port 8, flow dividers 9, flow restrictors 10 and a culture chamber body 11 allowing access to the cell culture slide for cell seeding, which has an area of 4 mm×13 mm. The dashed circle around the inlet and outlet port depicts the sealing area 8' of the cylinder of the interconnects. FIG. 1C shows a section in the middle of the microfluidic chip taken through the chamber. The height between the lower solid line and the dashed line depicts the raised inlet channels, whereas the upper solid line approximately depicts the culture chamber height, when the MPB was in perfusion configuration. Some embodiments may include MPBs similar in scale to the devices depicted in FIGS. 1A-1C. In various embodiments, a MPB may vary in size from the scale shown in FIGS. 1A-1C.

Figure 2:
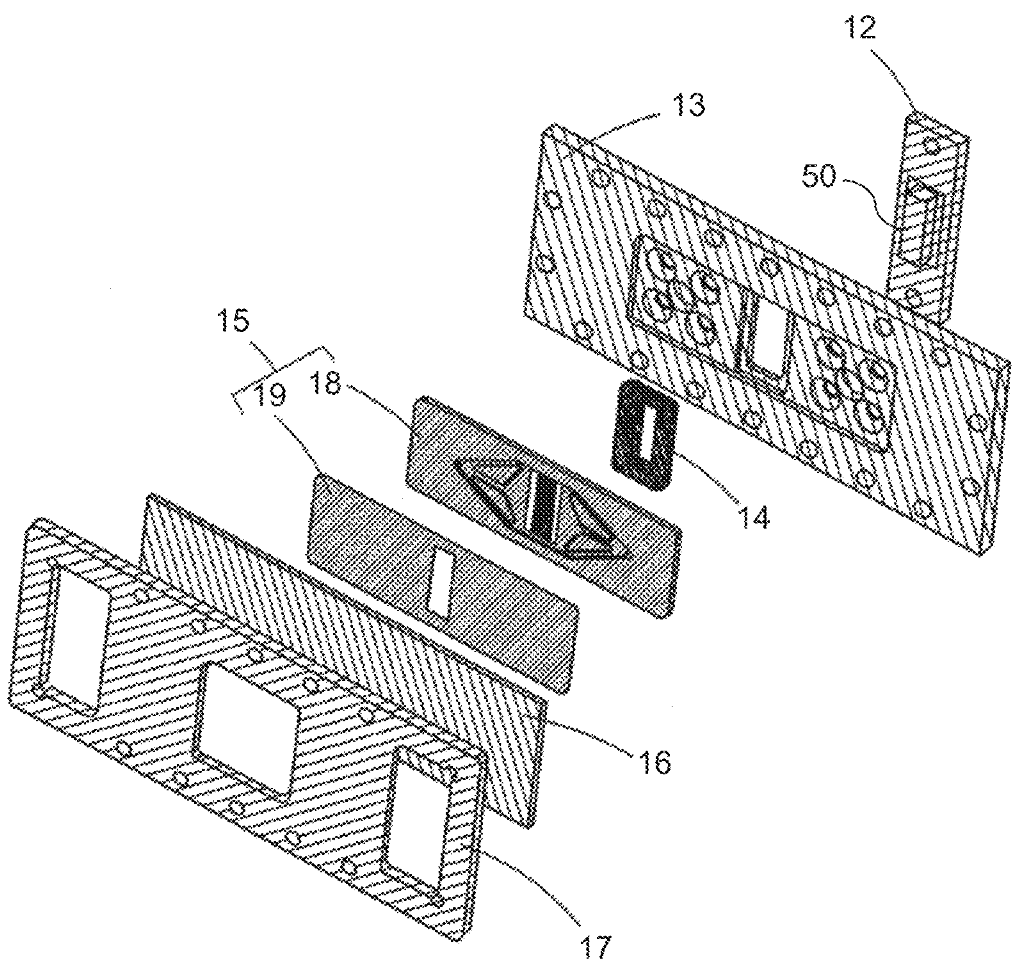
FIG. 2 is an exploded view of an embodiment of a microfluidic perfusion bioreactor (MPB) in a similar manner to FIG. 1A according to one embodiment of the present disclosure.

FIG. 2 shows an embodiment of solid models of a microfluidic perfusion bioreactor (MPB) similar manner to the MPB depicted in FIG. 1. FIG. 2 shows an exploded view of the MPB with its components such as a lid 12, interconnects for tubing (shown as 2 in FIG. 1A), a top plate 13, a gasket 14, a microfluidic chip 15 which is formed from two parts: a manifold layer 18; and a membrane 19, a cell culture slide 16 and a bottom frame 17.

Figure 3:
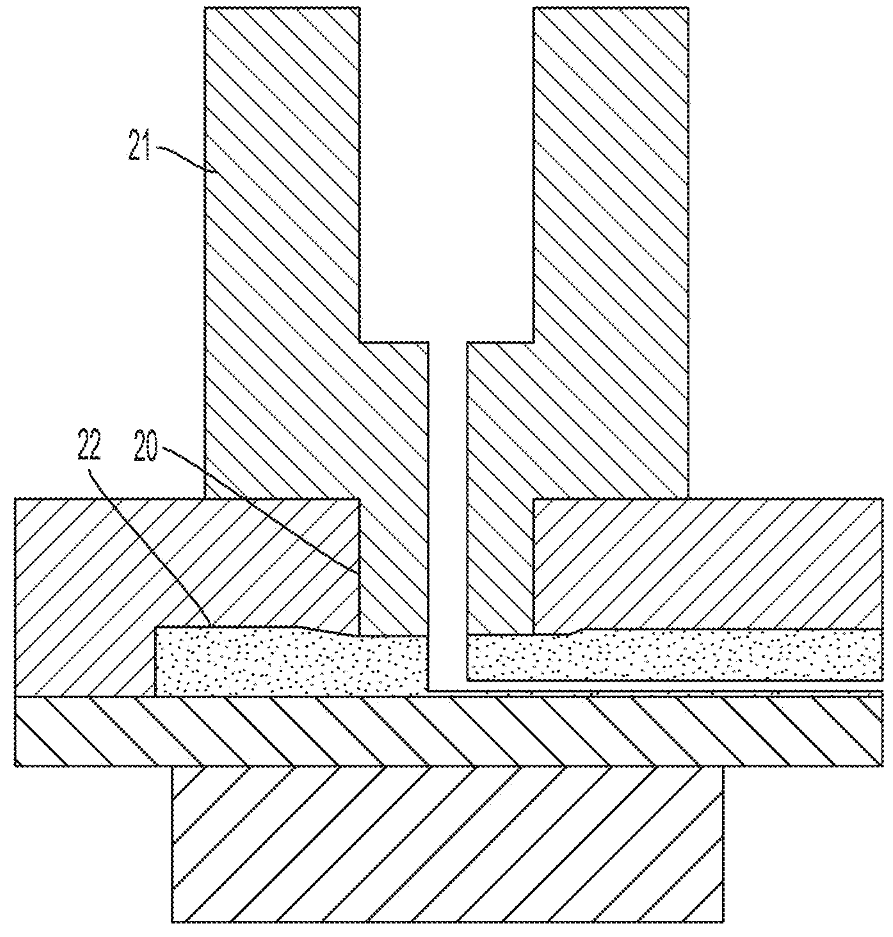
FIG. 3 shows a cross-sectional view of a microfluidic perfusion bioreactor taken along a plane in the interconnect region according to one embodiment of the present disclosure.

FIG. 3 shows a cross section taken through a MPB in the interconnect region. This figure shows projecting portion 20 on the interconnect 21 pressing into and deforming the microfluidic chip 22 in order to create a seal with microfluidic chip inhibiting and/or preventing leakage. In some embodiments, projecting portion 20 may be a cylinder, nipple and/or any other suitable structure known in the art.

Figure 4:
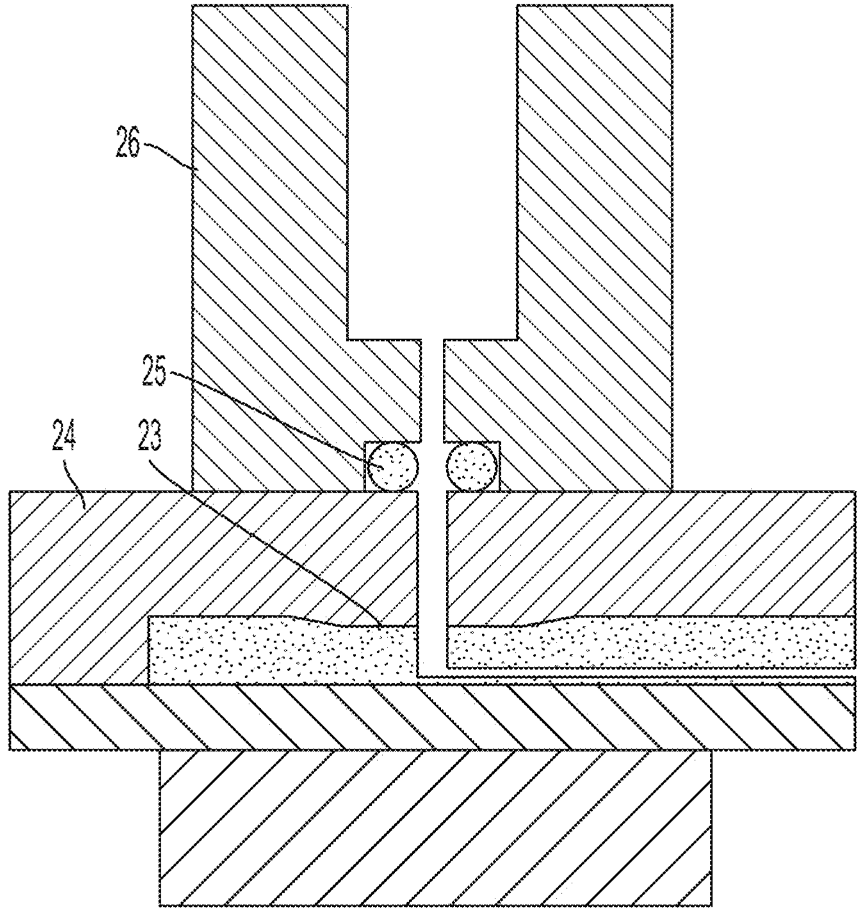
FIG. 4 depicts a cross-sectional view of an alternative embodiment of a microfluidic perfusion bioreactor taken along a plane in the interconnect region according to one embodiment of the present disclosure.

FIG. 4 shows a cross section of an alternative embodiment of a MPB in the interconnect region. In this embodiment, the projection 23 is on the top plate 24 of the MPB rather than on the interconnect itself. The interconnect 26 is mounted on the top plate and a seal is formed between the top plate and interconnect using a rubberized O-ring 25.

Figure 5:
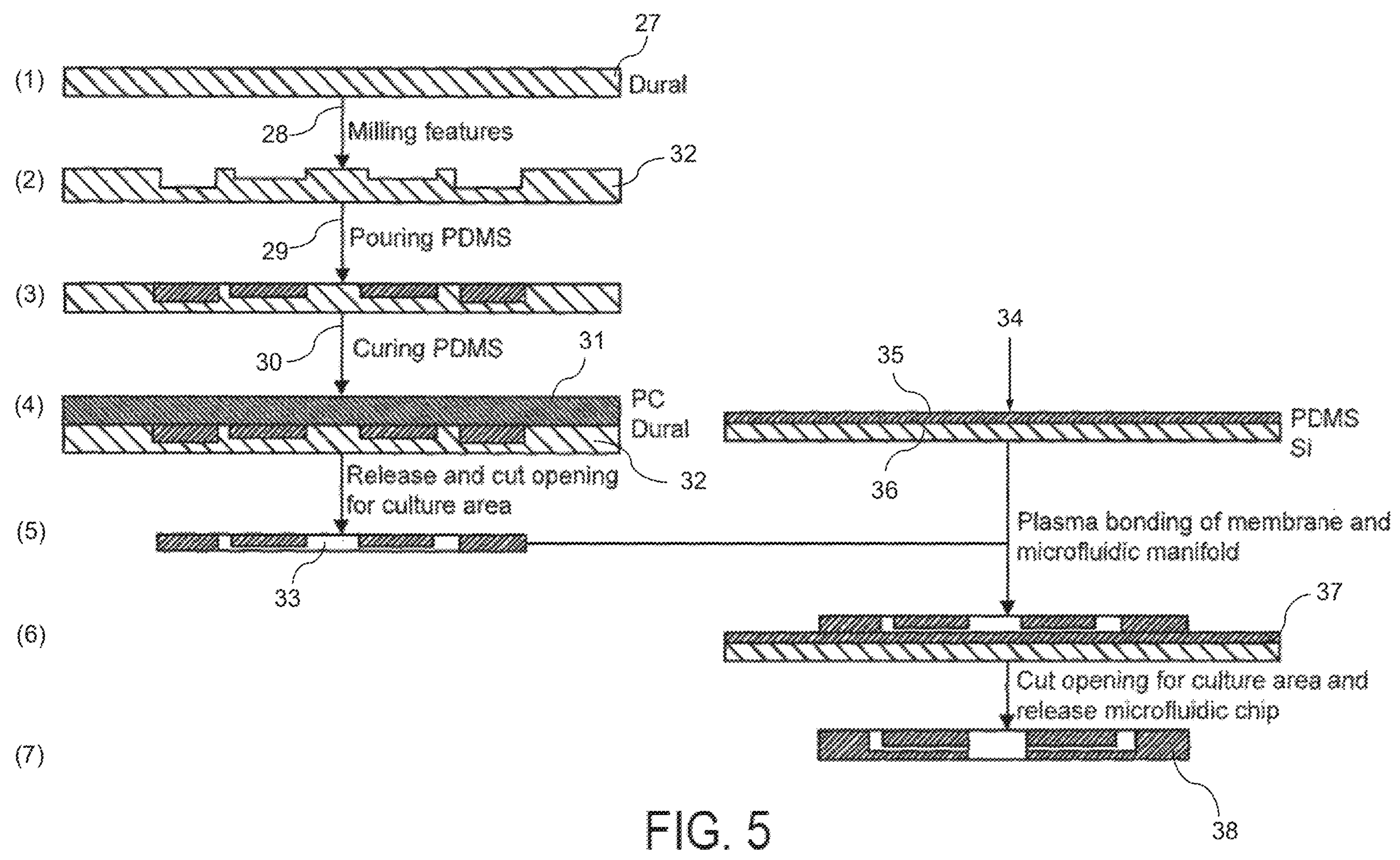
FIG. 5 depicts an embodiment of a fabrication process of a mold and a microfluidic chip created in the mold according to one embodiment of the present disclosure.

FIG. 5 shows a fabrication process of a mold and a microfluidic chip created in the mold. As shown in step (1) of FIG. 5, sheet 27 may be provided. Sheet 27 may include but is not limited to metals, alloys, such as Dural, and/or any material known in the art. As shown in FIG. 5, instep (2) sheet 27 was machined with a micromilling machine 28 to form a mold 32. In step (3) PDMS was poured 29 into the mold and then degassed. The PDMS was allowed to cure 30. As shown in step (4), a polycarbonate sheet 31 was placed on top of the mold 32 and clamped together. Concurrently, a silanized silicon wafer 36 was spin coated with PDMS 35 to form a membrane 34. The PDMS-coated wafer 34 and the clamped mold were then cured for 1 hour at 80° C. in an oven. Step (5) depicts the microfluidic manifold layer 33 released from the mold and the culture chamber body was cut out. In step (6), the microfluidic manifold layer 33 and the PDMS membrane 34 were exposed to an air plasma and immediately brought into contact for bonding to form structure 37. As shown in step (7), the membrane at the bottom of the culture chamber body was cut out and the microfluidic chip 38 was cut to shape and released from the wafer. In some embodiments, the rep-resentations depicted in FIG. 5 are not to scale.

Figure 6:
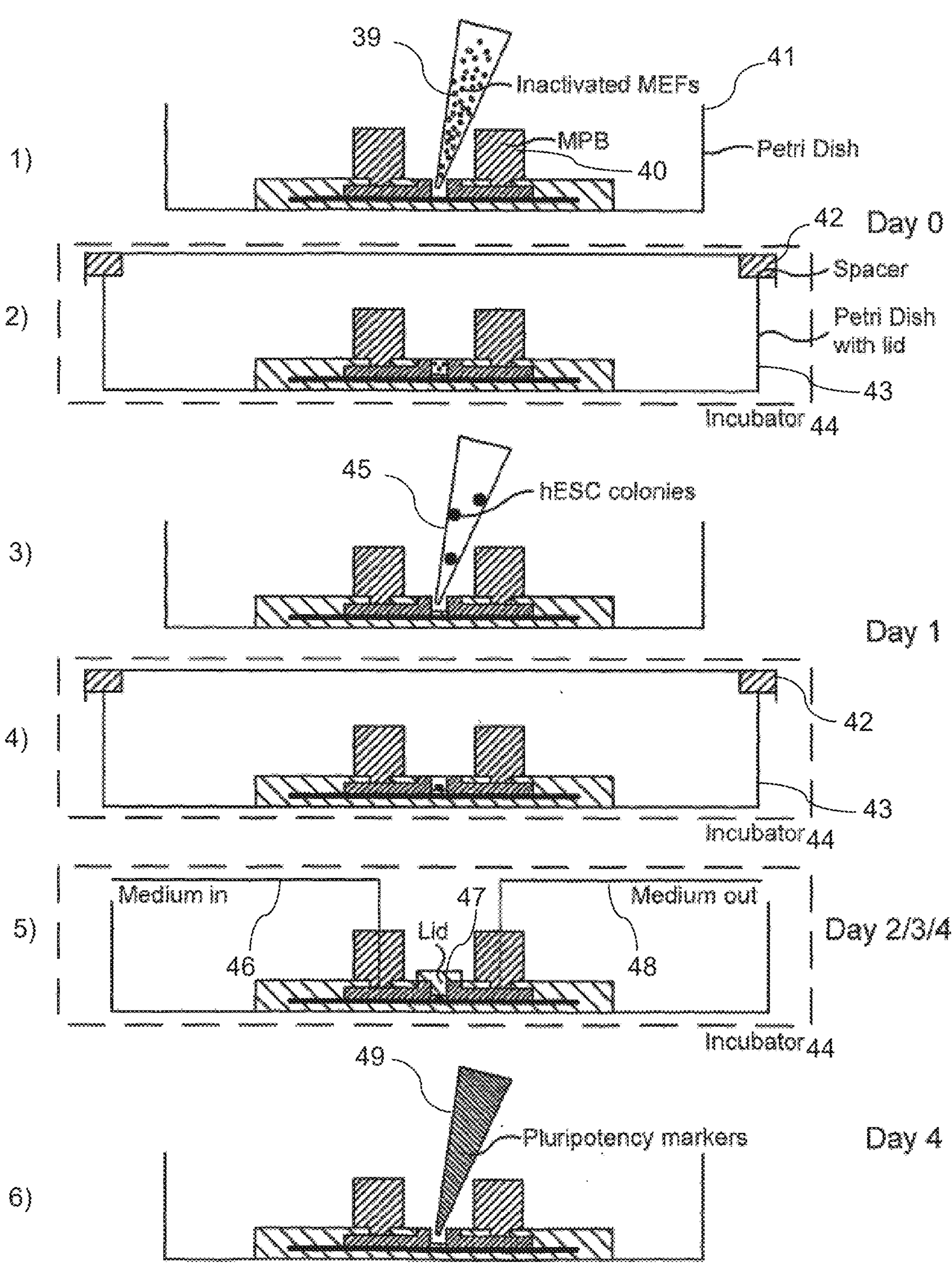
FIG. 6 is a schematic of the procedure for the mircrofusion perfusion bioreactor during seeding and perfusion according to one embodiment of the present disclosure.

FIG. 6 shows a schematic of the procedure for the MPB in seeding and perfusion configuration. On day 0, MPB 40 and a one well dish 41 were coated with 0.1% gelatine prior to seeding of the feeder layer. As shown in step (1) 20,000 inactivated murine embryonic fibroblasts (MEFs) 39 were seeded with a pipette directly into the cell culture chamber of the MPB and left over night to attach to the surface in an incubator. Step 2 of FIG. 6 depicts Petri dish 43 fitted with spacers 42 for gas exchange used to accommodate the MPB. The Petri dish with the MPB was kept in an incubator at 37° C., and 5% CO2 (b). On day 1, MEF medium was removed and hESC medium added 30 minutes before hESC colonies 45 were seeded. As shown in step (3) hESC colonies 45 were added into the culture area with a pipette (not shown), the Petri dish subsequently closed and the MPB placed back into an incubator 44. On day 2, shown in step (5) medium was aspirated and the culture chamber closed with a lid 47. Tubing 46, 48 was connected to the MPB and perfusion started using a syringe pump for two days in an incubator. On day 4 as shown in step (6), medium was aspirated, cells fixed and stained with pluripotency markers 49 to assess the effect of seeding and perfusion of hESC in a MPB. In some embodiment, dimensions of the various parts shown in FIG. 6 may vary.

Figure 7A:
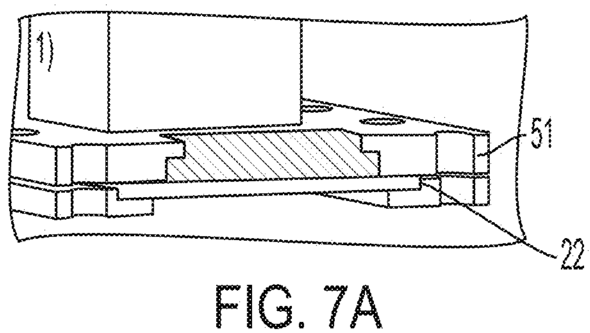
FIGS. 7A-C depict three cross sectional views of a microfluidic device and, in particular, the sealable port.
Figure 7B:
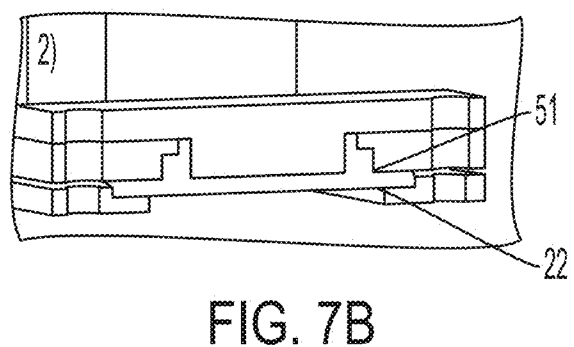
Figure 7C:
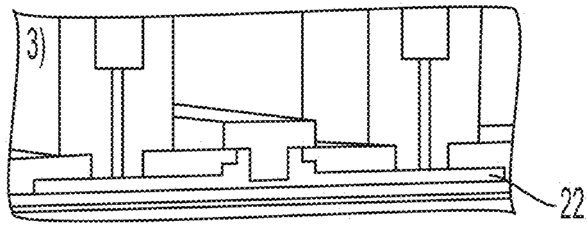

FIGS. 7A-C show three cross sectional views of a microfluidic device and, in particular, the sealable port 51. FIG. 7A depicts a microfluidic device 22 with the sealable port 51 open. FIG. 7B shows a microfluidic device 22 with the sealable port 51 closed. FIG. 7C depicts a microfluidic device 22 with the sealable port 51 closed in which the cross section is taken perpendicular to that of FIGS. 7A and 7B.

Figure 8:
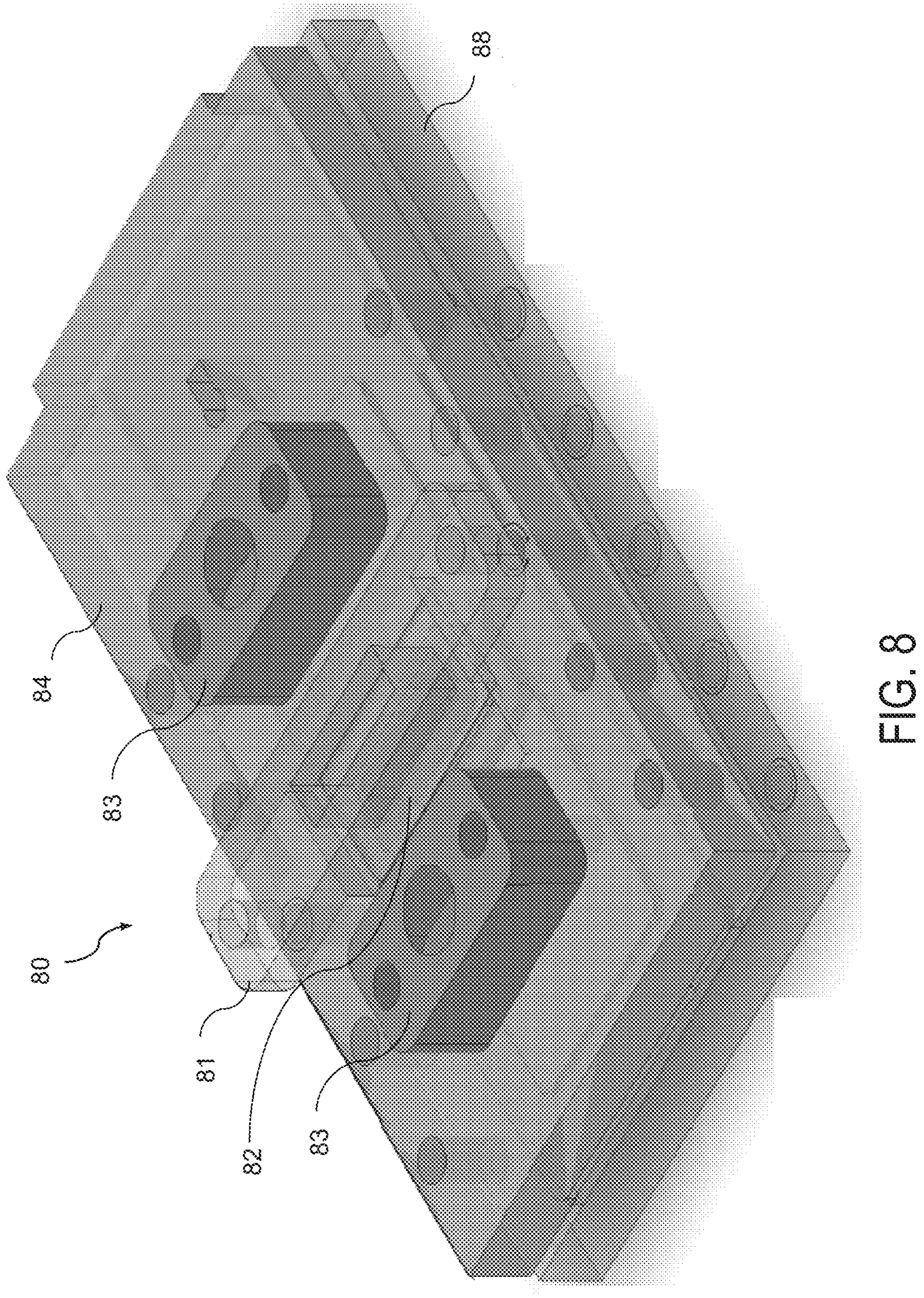
FIG. 8 illustrates a perspective view of another embodiment of a single assembly microfluidic perfusion bioreactor according to one embodiment of the present disclosure.
Figure 9:
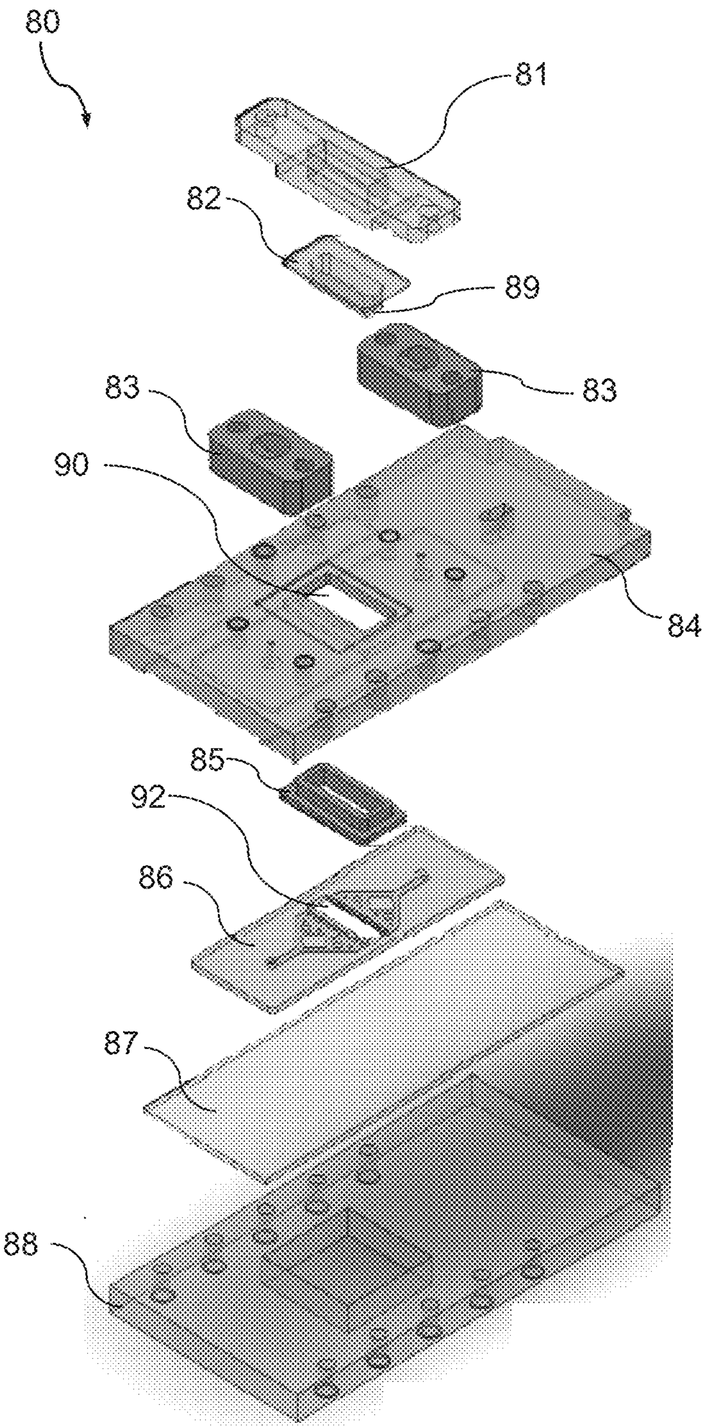
FIG. 9 depicts an exploded view of the microfluidic perfusion bioreactor of FIG. 8 according to one embodiment of the present disclosure.

FIGS. 8 and 9 illustrate another embodiment of a single assembly microfluidic perfusion bioreactor according to one embodiment of the present disclosure. In some embodiments, the single multiple assembly may be employed as a multiplexed device which may be utilized for parallelized execution of cell-based assays. Accordingly, the microfluidic perfusion bioreactor 80 may include gasket 81, lid 82, interconnects 83, top plate 84, gasket 85, microfluidic chip 86, slide 87, bottom plate 88, and lid 82. Microfluidic chip 86 may include a culture chamber 92.

A sealable port 90 may be provided in top plate 84 and configured for receiving lid 82 in a mated fit arrangement. Lid 82 is, therefore, appropriately dimensioned to be received by sealable port 90 such that when assembled thereto, lid 82 effectively seals sealable port 90. In this assembly, lid 82 may serve as a top or ceiling of culture chamber 92. In one embodiment, lid 82 may include a protrusion 89 which is appropriated dimensioned to extend from lid 82 to substantially fit the opening of culture chamber 92. In this manner culture chamber 92 may be sealed, and the top of culture chamber 92 may be formed by protrusion 89. The height of culture chamber 92 may be increased, for example, by reducing a dimension of protrusion 89 extending from lid 82. The material composition of lid 82 may include hard or soft materials such as PDMS (i.e., gas permeable). In some embodiments, lid 82 may serve and be employed as a gasket. Thus, lid 82 is configured to seal sealable port 90. In some embodiments, sealable port 90 may be regarded as part of a closure mechanism in combination with lid 82 for closing/sealing culture chamber 92.

Sealable port 90 may be configured to align with culture chamber 92 to prevent fluid and/or contents from escaping through sealable port 90, for example, when lid 82 is mated thereto in a closed position. Thus, the aforementioned closed position, may be established when lid 82 is inserted and seated within sealable port 90. Protrusion 89 of lid 82 may fill part of the volume of culture chamber 92, wherein the cross sectional dimensions of protrusion 89 are substantially the same as the inner dimensions of the side walls of culture chamber 92 such that protrusion 89 is in contact with the side walls of culture chamber 92. Disclosed embodiments provide that the lid 82 and the sealable port 90 are detachable from the microfluidic perfusion bioreactor.

Figure 10:
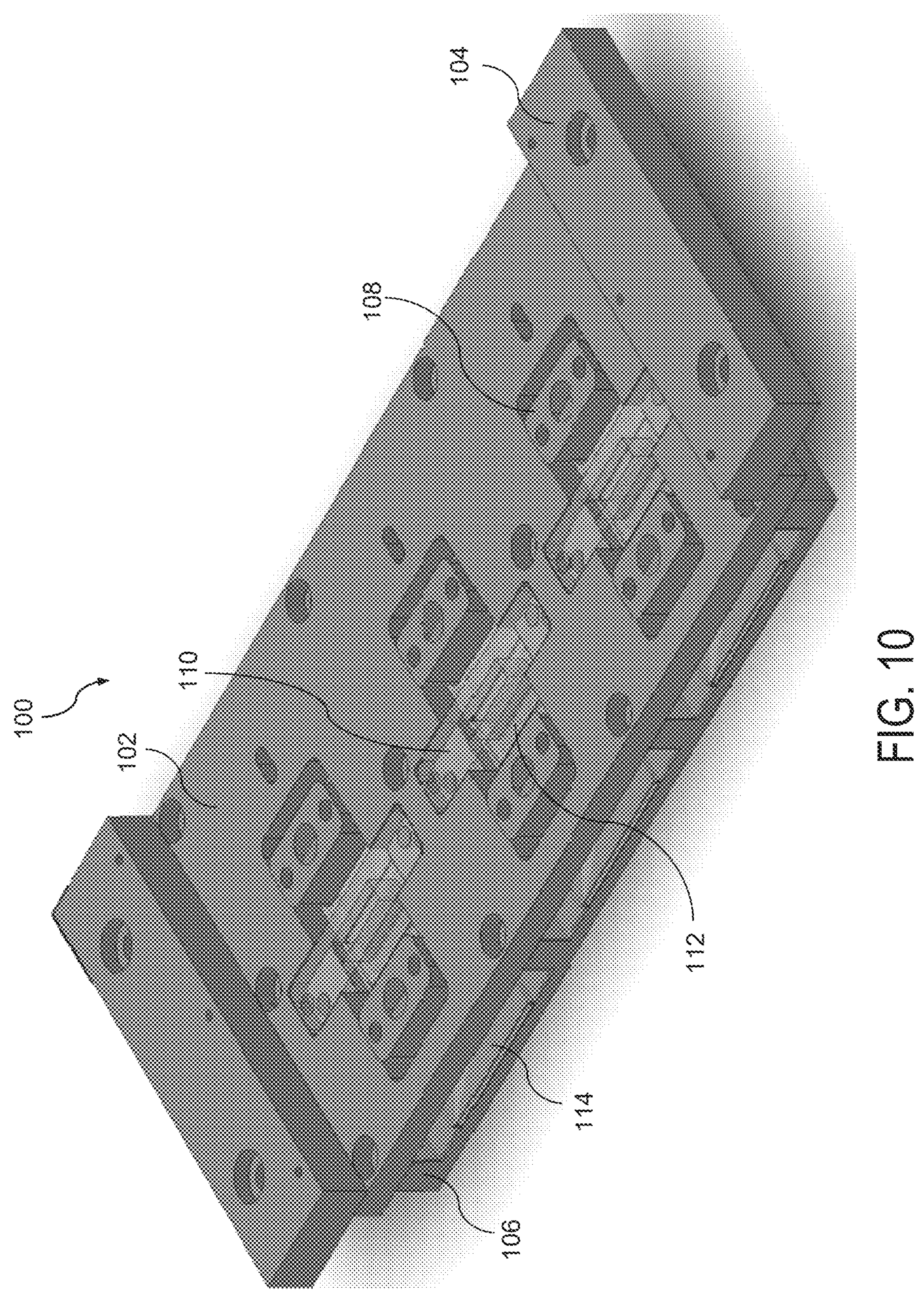
FIG. 10 illustrates a top perspective view of a multiple assembly embodiment of the microfluidic perfusion bioreactor of FIG. 8 according to one embodiment of the present disclosure.
Figure 11:
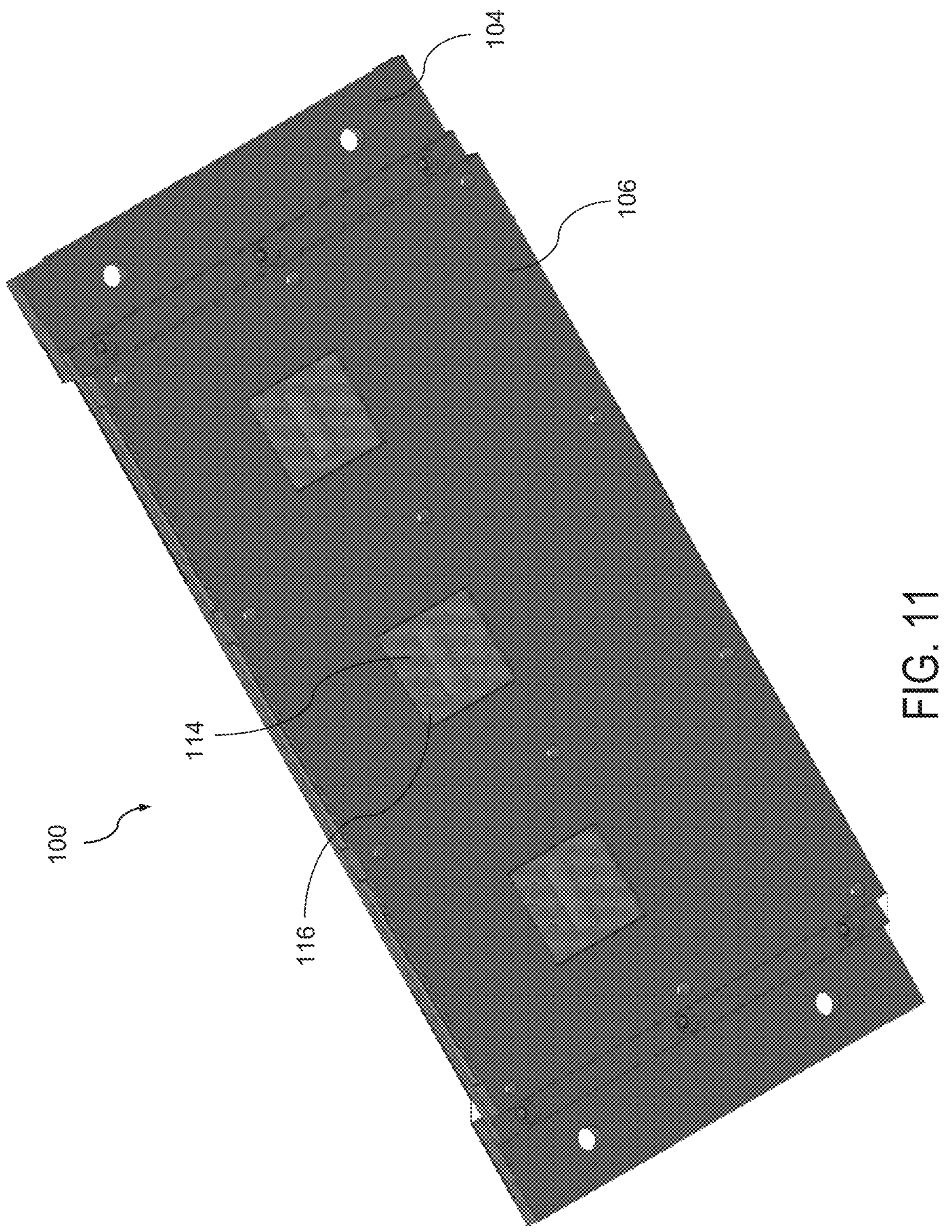
FIG. 11 illustrates a bottom perspective view of the multiple assembly embodiment of the microfluidic perfusion bioreactor of FIG. 10 according to one embodiment of the present disclosure.
Figure 12:
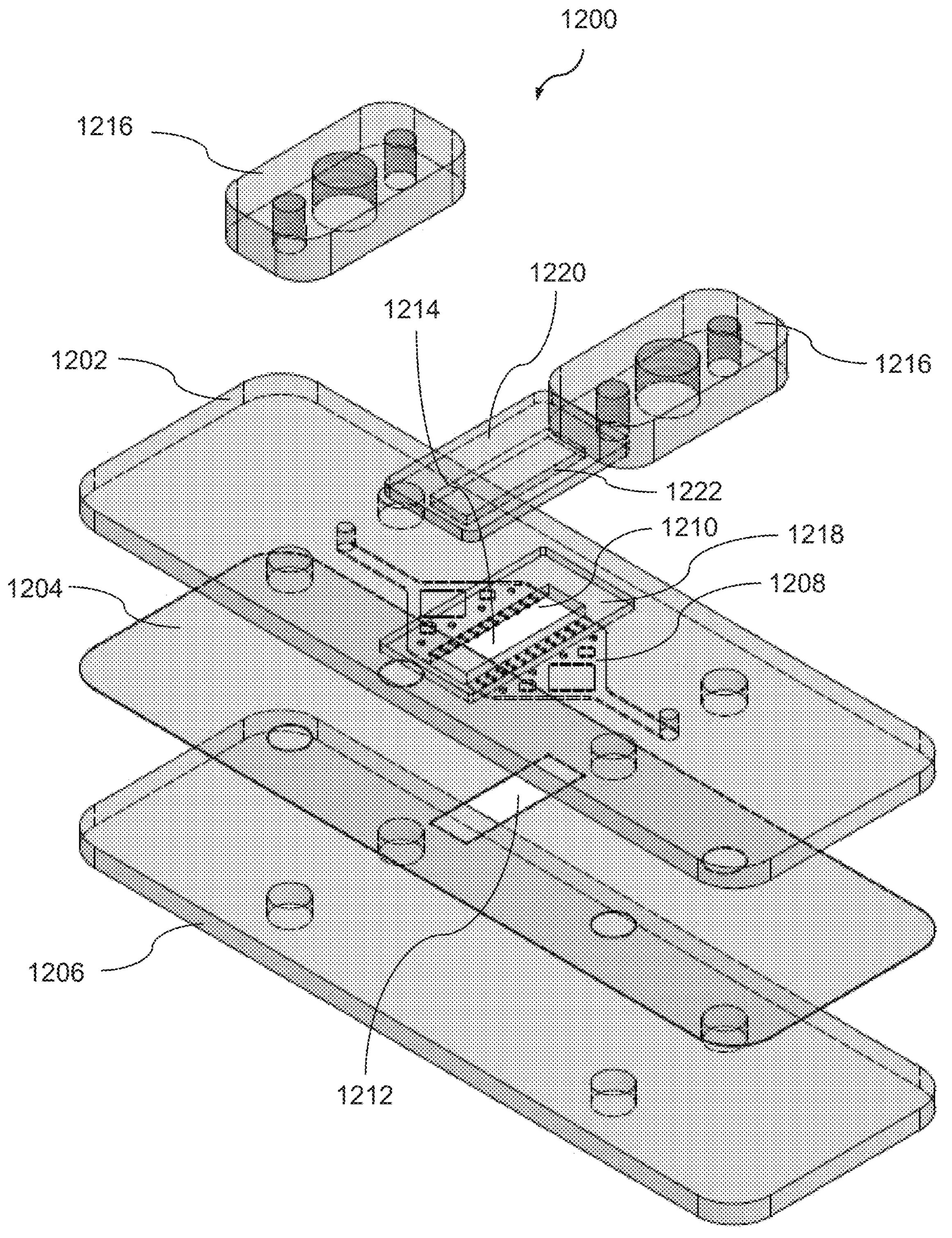
FIG. 12 illustrates an exploded view of an assembly of a microfluidic perfusion bioreactor according to another embodiment of the present disclosure.

The description and function of the aforementioned components microfluidic perfusion bioreactor 80 may include those previously described earlier and along with enhanced features as detailed below. FIGS. 10 and 11 illustrate a multiple assembly embodiment of a microfluidic perfusion bioreactor 100. In some disclosed embodiments, microfluidic perfusion bioreactor 100 is a multiple assembly of microfluidic perfusion bioreactor 80 of FIGS. 8-9. In some embodiments, the disclosed multiple assembly may be employed as a multiplexed devices which may be utilized for parallelized execution of cell-based assays. Accordingly, multiple assembled microfluidic perfusion bioreactor 100 top plate 102, holder bracket 104, bottom plate 106, interconnects 108, gasket 110, lid 112, slide 114, microfluidic chip 114. A window 116 may be disposed in bottom plate 106. The description and function of the aforementioned components of multiple assembled microfluidic perfusion bioreactor 100 may include those previously described earlier and along with enhanced features as detailed below.

FIGS. 12-15 provide another embodiment of the disclosed invention illustrated as a microfluidic perfusion bioreactor 1200. Microfluidic perfusion bioreactor 1200 may comprise a number of layers which may be bonded together to form a monolith or unitary structure. Accordingly, in one disclosed embodiment, microfluidic perfusion bioreactor 1200 may comprise a first layer 1202, a second layer 1204, and a third layer 1206. First layer 1202 may comprise microfluidic chip 1208 including an opening 1214 for forming a culture chamber 1210. Dimensions of culture chamber 1210 (i.e., the volume) may be adjusted, for example, by providing a recess 1212 in a surface of second layer 1204. Recess 1212 may be substantially aligned with opening 1214 to, thereby, adjust the dimensions of formed culture chamber 1210 such as increasing the volume area of culture chamber 1210 and or altering a position of cells disposed therein. In addition, and/or alternatively, a similar recess may be provided in third layer 1206 (not shown) to adjust a dimension of culture chamber 1210 such as increasing the volume area of culture chamber 1210 and or altering a position of cells disposed therein. Again, any recess formed, for example, in third layer 1206 will substantially align with opening 1214 to, thereby, adjust the dimension of formed culture chamber 1210.

The inclusion of recess 1212 to adjust a dimension of culture chamber 1210 allows alternate positioning, for example, of cells disposed within culture chamber 1210. Thus, by altering the positioning of the cells, the main plane of the fluid flow may not readily come into direct contact with the cells (such as along the side of the cells). Rather, with the cells sitting within the recess, the main plain of the fluid flow may be spaced from the cells and flow, for example, above the cells. For example, cells within recess 1212 may be positioned lower within culture chamber 1210 such that contact fluid flows substantially over the cells. In contrast, without the recess 1212, contact fluid may be more prone to contact cells disposed within culture chamber 1210 at a level occurring, for example, from the side of the cells. Thus the fluidics is slightly elevated such that the flow substantially flows over the disclosed cells rather than directly at the cells.

Figures 16, 17:
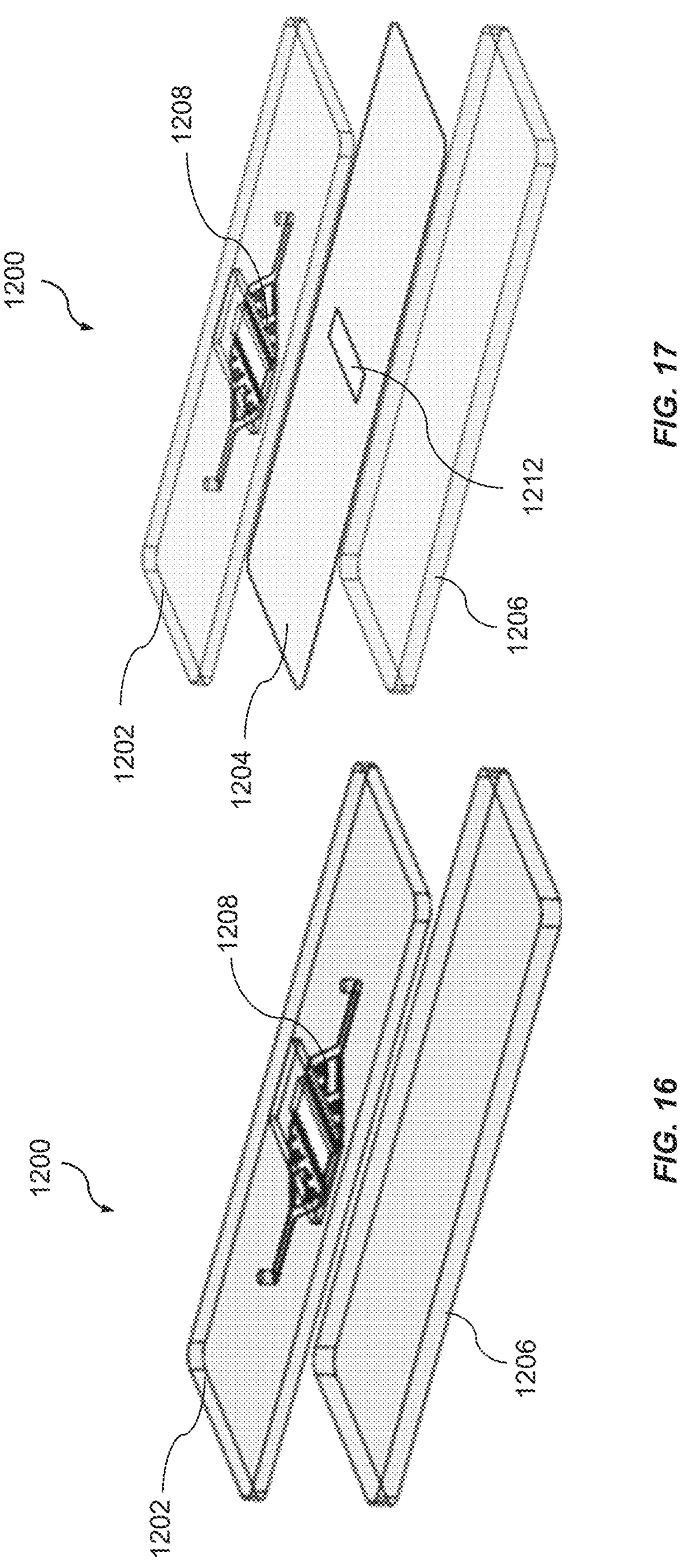
FIG. 16 illustrates a two-layer design of the microfluidic perfusion bioreactor of FIG. 12 according to one embodiment of the present disclosure.
FIG. 17 illustrates a three-layer design of the microfluidic perfusion bioreactor of FIG. 12 according to one embodiment of the present disclosure.

As previously mentioned, disclosed embodiments provide that microfluidic perfusion bioreactor 1200 may comprise some or all of the layers 1202, 1204, and 1206 to form a monolith or unitary structure. In some embodiments, some of the aforementioned layers may be excluded, and some layers may be combined to form a single layer. Thus, in some embodiments, second layer 1204 and third layer 1206 may be formed as one part. In addition, and/or alternatively, recess 1212 may be formed in only second layer 1204 and/or in third layer 1206 (not shown). In some disclosed embodiments, second layer 1204 may be excluded and the microfluidic perfusion bioreactor 1200 may comprise only layers 1202 and 1206. In this design, a recess 1212 may or may not be included in layer 1206 (not shown). Thus, microfluidic perfusion bioreactor 1200 may be configured having a two-layer configuration or a three-layer configuration as shown, for example in FIGS. 16 and 17, respectively. It is readily appreciated that more than three layers may be provided and implemented in the final design configuration of the disclosed microfluidic perfusion bioreactor 1200. Again, any amount of prescribed layers may be formed into a single layer monolith or unitary structure such as through an appropriate bonding process. Also, more recesses 1212 may be provided in one or more of the aforementioned layers, for example, to alter a final dimension of the culture chamber 1210 as described above.

First layer 1202 may contain the channel arrangement and structure of microfluidic chip 1208 (e.g., with inlet/outlet ports, flow dividers, flow restrictors and a culture chamber body). Materials of first layer 1202, second layer 1204, and third layer 1206 may be selected from hard polymer materials (e.g., PMMA, COP, COC, etc.) or thermoplastic polymers or polystyrene (PS). In addition, one or more interconnects 1216 may be assembled in connection with first layer 1202.

A sealable port 1218 may be provided in layer 1202 and configured for receiving a mated lid 1220. Lid 1220 is, therefore, appropriately dimensioned to be received by sealable port 1218 such that when assembled thereto, lid 1220 effectively seals sealable port 1218. In this assembly lid 1220 may serve as a top or ceiling of culture chamber 1210. In one embodiment, lid 1220 may include a protrusion 1222 which is appropriated dimensioned to extend from lid 1220 to substantially fit opening 1214 of culture chamber 1210. In this manner culture chamber 1210 may be sealed, and the top of culture chamber 1210 may be formed by protrusion 1222. The height of culture chamber 1210 may be increased, for example, by reducing a dimension of protrusion 1222 extending from lid 1220. The material composition of lid 1220 and sealable port 1218 may include hard or soft materials such as PDMS (i.e., gas permeable) or hard polymer. In some embodiments, lid 1220 may serve and be employed as a gasket. Thus, lid 1220 is configured to seal sealable port 1218. In some embodiments, sealable port 1218 may be regarded as part of a closure mechanism in combination with lid 1220 for closing/sealing culture chamber 1210. The closed configuration of lid 1220 sealed with sealable port 1218 provides a substantially hermetic seal. In some configurations, this is considered a reversibly hermetic sealable port 1218, since lid 1220 is configured to be removed from sealable port 1218 in an open configuration.

Sealable port 1218 may be configured to align with culture chamber 1210 to prevent fluid and/or contents from escaping through sealable port 1218, for example, when lid 1220 is mated thereto in a closed position. Thus, the aforementioned closed position, may be established when lid 1220 is inserted and seated within sealable port 1218. Protrusion 1222 of lid 1220 may fill part of the volume of culture chamber 1210, wherein the cross sectional dimensions of protrusion 1222 are substantially the same as the inner dimensions of the side walls of culture chamber 1210 such that protrusion 1222 is in contact with the side walls of culture chamber 1210. Disclosed embodiments provide that the lid 1220 and the sealable port 1218 are detachable from the microfluidic perfusion bioreactor. The remaining structure of the disclosed microfluidic perfusion bioreactor 1200 may comprise a unitary member or monolith comprising, for example, one or more bonded layers.

As described herein, some embodiments of the disclosed a microfluidic device may include a chamber, for example, having a fluid inlet, a fluid outlet and a sealable port. The fluid inlet and the fluid outlet may be positioned to direct fluid flowing from the fluid inlet to the fluid outlet through the chamber. The sealable port may be aligned with the chamber to allow insertion of material into the chamber or extraction of material from the chamber when the sealable port is open, and to inhibit and/or prevent fluid from escaping through the sealable port when the port is sealed. In accordance with additional embodiments, supplementary structure may be added and configured to lid 1220 such as fluidic ports on each side of the lid.

The sealable port allows material to be placed directly into or removed from the chamber of the device. For example, the sealable port permits easy and gentle seeding of cells and extra-cellular matrix (ECM) compounds into the chamber, the perfusion of the cells and, subsequently, their easy and gentle uptake from the chamber. Alternatively, the port allows the loading and removal of beads or polymer monoliths, for example, for enzymatic assays and arrays of pillars such as those made of different materials and potentially surface-modified to enable enzyme immobilization. The placement of material directly into the chamber and the removal of material from the chamber of the device is done from the exterior of the device, for example, manually using a pipette or other suitable device. This means that the material can be placed directly into the chamber in the precise position that is required for carrying out a particular function. An advantage of the sealable port is that it allows a pre-determined and/or an exact quantity of material to be placed in the chamber which may be crucial for accurately performing assays or tests. Further, this avoids the problems associated with flushing the material into the chamber from an upstream inlet. For example, the problem of high undefined shear stress on the cells as they are flushed into the chamber is avoided. Another concern may include the introduction of extra-cellular matrices (ECM) in such a way that only the chamber or a specific portion of the chamber is coated with the ECMs or other coating. Further, the sealable port may improve the macro-to-micro interface as the port can be opened and closed repeatedly so that different materials can be inserted into and removed from the chamber at will. This provides the device with greater flexibility which enhances the achievable degree of complexity and thus the degree of functionality.

For instance, the open configuration of the sealable port may allow for the static culture of cells (e.g., with a culture medium fluid overlay of about 2-3 mm). In addition, the open configuration may also enable coating of a growth substrate, inoculation, seeding, cell recovery, and removal of material or harvesting. The closed configuration of the sealable port may allow for perfusing a microfluidic culture, for example, at a normalized microfluidic chamber height (e.g., approximately 0.45-0.5 mm). The disclosed device may also serve as a test-bed for wound-healing assays (using, for example, the open and closed configuration of the disclosed invention). In some disclosed embodiments, the sealable port may be configured to insert an array of pillars with immobilized enzymes for enzyme reactions. Some disclosed materials of the aforementioned pillars may include: glass, silicon, and/or other modified surface. In other embodiments, the sealable port may be configured to introduce bags with beads where enzymes are immobilized and/or introduce optical sensors/biosensors with the lid. Thus, in one embodiment, a coating containing the optical sensor may be applied to the lid.

In the context of this invention, the term "microfluidic device" means a miniaturized device through which fluids flow in a controlled manner and in which fluids are geometrically constrained to a small, typically sub-millimeter, scale. These parameters may vary. For example, in some embodiments, fluids may be geometrically constrained on an order larger than a millimeter (such as along the in x and y axis). Generally, channels in a microfluidic device may have dimensions in the order of tens to hundreds of microns or larger and it is through these channels that fluids, normally liquids, flow. A person skilled in the art would appreciate what is meant by this term.

The chamber can be any suitable size and shape so that it can carry out its particular function. For example, in one embodiment, the device is used for culturing cells. Therefore, the chamber is sized so that it can contain a number of cells whilst still allowing fluid to flow through the chamber from the fluid inlet to the fluid outlet in a laminar flow fashion. In such an embodiment, the volume of the chamber may be between about 1-26,000 $mm^3$. In some disclosed embodiments, a volumetric working range of the chamber includes about 1-500 $mm^3$. Disclosed embodiments also include a preferred volumetric range of the chamber about 1-160 $mm^3$. More preferably, the volume of the chamber will be between about 1 $mm^3$ and about 50 $mmn^3$, more preferably still, between about 10 $mm^3$ and about 40 $mm^3$, and most preferably, between about 20 $mm^3$ and about 30 $mm^3$. A suitable chamber might have a length of between about 1 mm and 8 mm, a width of between about 5 mm and about 18 mm and a height of between about 0.2 mm and about 1 mm. In some applications, the chamber may have a length of up to about 150 mm, a width of up to about 150 mm, and a height of up to about 1 mm. In other applications, the dimensions of the chamber may be adjusted, for example, to include a length of about 8 mm, a width of about 150 mm, and a height of 1 mm. However, a preferred chamber has a length of about 4 mm, a width of about 60 mm and a height of about 0.5 mm. A chamber of this size is particular useful for culturing hESC on a bed of feeder cells. The disclosed chamber may be any suitable shape. For example, it may be cuboidal, oval, elliptical, disc shaped or any other suitable geometrical shaped configuration to perform its particular function. In some preferred embodiments, the chamber is cuboidal. Some preferred embodiments provide a chamber having a cross sectional area perpendicular to the flow of fluid of at least about 4 $mm^2$, more preferably, at least about 5 $mm^2$ and, most preferably, at least about 6 $mm^2$. As discussed below, this helps to reduce the flow velocity and shear stress in the chamber.

While aspects of the disclosed microfluidic device enable the culturing and processing of cells (i.e., the processing and production of cells), and generally the handling and treatment of cells to create cellular products or products from cells, it is important to appreciate that the disclosed chamber may receive other additional types of material(s) other than cells. For example, disclosed embodiments of the chamber may be configured to receive one or more materials including: cells or cell clusters, cellular grafts, or cell organoids or cell embroyids, or cell spheroids or other 3D cell constructs or indeed any 3D cell structure mimicking tissue and organs (including the required scaffolds); or small organs like adrenals, suspended or adherent cells microbial cells such as biofilms enzymes including any support structures for immobilized enzymes, such as, but not limited to, organic and inorganic supports, using any kind of reversible or irreversible enzyme immobilization method, extra-cellular matrices such as extracellular macromolecules and minerals, such as collagen, enzymes, glycoproteins and hydroxyapatite that provide structural and biochemical support to surrounding cells. In addition, any kind of proteins or gels may be applied as surface modification techniques to the chamber, such as for example the surface of the bottom chamber, to optimize operating conditions by tailoring the physical, chemical or biological characteristics of the chamber surface.

In some embodiments, the size of the chamber can have an important effect on the conditions inside the chamber. As fluid flows from the fluid inlet to the fluid outlet, the material in the chamber will experience a shear stress as a result of the flow velocity of the fluid around and over the material. Given a constant flowrate, increasing a channel's height and width decreases shear stress as the flow velocity is decreased due to the greater cross sectional area of the channel. Therefore, for the microfluidic device, the larger the chamber dimensions perpendicular to the flow of the fluid, the lower the shear stress that the material in the chamber experiences due to a decreased flow velocity. For cell cultures, the flowrate can be important as it must be high enough to ensure that the cells obtain enough nutrients, such as oxygen, from the medium in order to keep them healthy. By having a chamber with a large area perpendicular to the flow of fluid, it is possible to have a relatively high flowrate but a relatively low flow velocity and, therefore, shear stress. Therefore, the size of the chamber is an important consideration.

The above description relates to the microfluidic device having the sealable port in a sealed position. In one embodiment, the volume defined by the chamber may be greater when the sealable port is not in the sealed position, i.e., when the sealable port is open. This can be achieved by the lid having a protrusion which fills part of the volume of the chamber. The advantage of this is that, in certain circumstances, the sealable port can be left in an open position, so that the chamber has a larger volume. For example, when the microfluidic device is used for cell culture, cells can be seeded into the chamber. Having the port open allows more medium to be contained in the chamber, thereby ensuring that the cells are kept in a viable condition. The sealable port can be sealed, such as by mating with the disclosed lid, at a later stage.

In some embodiments, the fluid inlet and the fluid outlet are positioned in such a way so that fluid flowing from the fluid inlet to the fluid outlet may be directed through the chamber. As a result of the fluid flowing through the chamber, material placed in the chamber will come into contact with the fluid as the fluid is passing through the chamber. This ensures that the material is exposed to any substance (e.g. chemicals, reagents, nutrients, enzymes, antibodies, etc.) contained in the fluid. Preferably, the fluid inlet and the fluid outlet are positioned on opposite sides of the chamber. In some embodiments, the fluid inlet and outlet are positioned on the largest face or surface of the chamber. This may ensure that any change in the fluid composition entering the chamber, for example, the introduction of a chemical, is quickly dispersed to the whole chamber and also to any material contained therein. Further, having the inlet and outlet positioned on opposite sides of the chamber may improve or maintain the homogeneity of the flow.

In a preferred embodiment, the fluid inlet and the fluid outlet are positioned so that a material containment portion of the chamber is substantially unaffected by the flow of fluid through the chamber. The material containment portion of the chamber is simply a portion of the chamber which is for containing material which is placed in the chamber. For example, this may simply be the bottom of the chamber. Material placed in the containment portion of the chamber is substantially unaffected by the flow of the fluid in that it is not subjected to a significant shear stress as a result of the flow of the fluid. The flow of fluid is not directed through this containment portion. This is important for cell culture and, in particular, for sensitive cell types like hESC (i.e., human embryonic stem cells). For example, the fluid inlet and the fluid outlet may both be positioned in a top portion of the chamber. In some embodiments, the fluid inlet and fluid outlet are positioned in the top three quarters of the chamber. In this way, material placed in a bottom portion, for example, the bottom quarter of the chamber, is not substantially affected by the flow of fluid as the majority of the flow passes over the top of the material, thus reducing the shear stress that the material experiences. In some embodiments, the fluid inlet and fluid outlet are positioned opposite each other on the side walls of the chamber. Preferably, they are positioned in the top half of the chamber. In various embodiments, the fluid inlet and outlet may be positioned about 120 μm above the base of the chamber. Preferably, the fluid inlet and the fluid outlet are aligned with the top of the chamber. When the material containment portion is at the base of the chamber, the fluid inlet and outlet may be positioned in range from between about 10 μm to about 1 mm above the base of the chamber and, preferably, in a range between about 50 μm to about 300 μm above the base of the chamber. Effectively, this gives a material containment portion having a depth in a range from about 10 μm to about 1 mm and, preferably, having a depth in a range from about 50 μm to about 300 μm.

The reason behind this is that in microfluidic systems fluid flows in a substantially laminar manner. Therefore, material not directly in the path of the flow experiences a much reduced flow velocity and so a much reduced shear stress. Preferably, material placed in the containment portion of the chamber which is substantially unaffected by the flow of fluid experiences a shear stress of less than about 0.001 dyne/$cm^2$ and, more preferably, less than about 0.0001 dyne/$cm^2$.

The fluid inlet and fluid outlet can be any suitable conduit or opening to allow fluid to enter and exit the chamber. A person skilled in the art would be fully aware of standard fluid inlets and fluid outlets used in microfluidics which could be used in the present disclosure. Preferably, a liquid such as culture medium pass through the chamber from the fluid inlet to the fluid outlet.

The fluid inlet and fluid outlet can be any suitable size or shape. In one embodiment, the fluid inlet, fluid outlet or both are relatively wide or large compared to the chamber. For example, the fluid inlet and/or fluid outlet may have a width which is the same as the width of the chamber. The advantage of having a relatively large fluid inlet and/or outlet is that, for a given flowrate, the flow velocity of the fluid entering the chamber will be relatively low so that the contents of the chamber experience a relatively low shear stress. Preferably, when the chamber is cuboidal, the fluid inlet forms at least about 10% of the area of one side of the chamber. More preferably, the fluid inlet forms at least about 15% of the area of one side of the chamber, more preferably still, at least about 20% and, even more preferably, at least about 30%. Alternatively, the fluid inlet may form between about 10% and about 70% of the area of one side of the chamber, more preferably, between about 15% and about 60% and, even more preferably, between about 20% and about 50%. The fluid outlet and the fluid inlet may be the same size and shape or may be different. The above values and ranges for the size of the fluid inlet are equally applicable to the size of the fluid outlet.

Where the chamber has a curved outer wall, for example where it is disc shaped, the fluid inlet may be positioned anywhere on the curved wall. Where the chamber is cuboidal, that is its outer wall has a number of flat faces joined at the edges of the cuboid, the fluid inlet may be positioned on one of the faces, or over an edge joining two faces. Preferably, it is positioned on one of the faces. Preferably, it is positioned on the widest face. The outlet may be similarly positioned.

The device may have a plurality of fluid inlets and/or fluid outlets. These may be the same size or different sizes. They may carry the same fluid or they may carry fluids with different compositions. If there is a plurality of fluid inlets and/or outlets the above paragraph relating to the area of the chamber side that is formed by the fluid inlet/outlet, relates to the plurality of inlets/outlets, i.e. the fluid inlets preferably form at least about 30% of the area of one side of the chamber, etc.

In one embodiment, a conduit carries fluid to the fluid inlet. Preferably, the conduit increases in cross sectional area as it approaches the fluid inlet. For example, both the height and width of the conduit may increase to form a cone shape. Preferably, the conduit only increases in width as it approaches the fluid inlet. This increase in cross sectional area has the effect of decreasing the fluid velocity in the conduit so that when the fluid enters the chamber through the inlet, the material in the chamber is not subjected to a high shear stress. This is especially the case in microfluidics where the conduit may have dimensions of tens or hundreds of microns. For example, the conduit may increase in width from about 200 μm to about 13 mm where it enters the chamber. Where the conduit increases in width or size, the fluid inlet is preferably positioned on the widest face of the chamber. The fluid outlet can also have a similar feature so that a conduit decreases in cross sectional area as it becomes more distant from the fluid outlet.

In a preferred embodiment, the fluid inlet, the fluid outlet or both comprise one or more flow restrictors. These are thin members which partially obstruct the fluid inlet/outlet so that a plurality of channels are formed in the fluid inlet/outlet and which have the effect of at least partially homogenizing the flow velocity of the fluid across the entire width or area of the fluid inlet/outlet. This has the effect of at least partially homogenizing the shear stress profile across the chamber. This is especially important where the fluid inlet, fluid outlet or both are relatively wide or large compared to the chamber. Preferably, there is a plurality of flow restrictors. The larger the number of flow restrictors, the more homogenous the flow velocity, and therefore the shear stress profile, will be. Preferably, the flow restrictors are equally spaced in the fluid inlet/outlet so that the channels formed thereby are of equal size. This helps to ensure that the flow velocity is as uniform as possible.

Generally, in microfluidic devices, fluid is carried to a fluid inlet and away from a fluid outlet in channels or conduits which are of several microns to hundreds of microns in size. In some embodiments, the device may include a conduit to carry fluid to the fluid inlet and a conduit to carry fluid away from the fluid outlet, one or both of the conduits may contain one or more flow dividers. In some embodiments, one or both of the conduits contain a plurality of flow dividers. Flow dividers work in a similar manner to flow restrictors and result in the fluid having a more uniform flow velocity when it reaches the fluid inlet, thus resulting in the fluid having a more uniform flow velocity as it enters the chamber. Preferably, the flow dividers are positioned in the portion of the conduit which increases in size as it approaches the fluid inlet. Similarly, they can be positioned in the decreasing conduits leaving the fluid outlet.

The sealable port is aligned with the chamber to allow insertion of material into the chamber or extraction of material from the chamber when the sealable port is open, and to inhibit and/or prevent fluid escaping through the sealable port when the port is sealed. Preferably, the fluid is liquid. The sealable port can be any suitable size or shape as long as it allows easy insertion and extraction of material into and out of the chamber. The size of the port will depend, in part, on the size of the chamber. The port can be positioned at any suitable point in/within the chamber. In some disclosed embodiments, the sealable port may form the uppermost portion of the chamber. In one embodiment, the sealable port forms a lid of the chamber so that the uppermost portion of the chamber is formed by the sealable port. The sealable port may be sealed in any suitable way. For example, the sealable port may be sealed using a gasket formed from a deformable material such as rubber or silicone.

In one embodiment in which liquid passes through the chamber, the sealable port may comprise a gas permeable membrane to allow gas such as oxygen or carbon dioxide to pass into the chamber. In this embodiment, when liquid such as culture medium is not flowing through the chamber, oxygen can pass into the chamber so that any cells have the required level of oxygen to keep them healthy. In such an embodiment, the sealable port stops any liquid escaping from (or entering) the chamber but allows gas to pass into the chamber.

In some embodiments of the invention, the chamber, fluid inlet and outlet, and any conduits connected to the fluid inlet and outlet may be encapsulated. For example, they may be encapsulated in a frame or housing. However, in one embodiment, a conduit which connects to the fluid inlet may be made of a gas permeable material, such as PDMS, and at least partially exposed to allow gas to enter the conduit and any liquid contained therein. In such an embodiment, the conduit is for carrying liquid to the fluid inlet. This allows gas such as oxygen to enter the liquid being carried in the conduit so that the gas passes into the chamber with the liquid.

The base of the chamber can be formed from a substrate for supporting biological material. The substrate can be any suitable tissue culture substrate such as glass or polystyrene. Preferably, the substrate is a standard substrate and the chamber is formed on at least a portion of the substrate. For example, suitable standard substrates may comprise glass or polystyrene microscopy slides or culture plates.

The substrate allows biological material to be attached thereto. For example, cells, antibodies, proteins such as enzymes and ECM compounds can be attached to the substrate.

The fact that the substrate is detachable from the device facilitates the comparison of microfluidic assays with traditional assays, for example, the comparison of traditional cell culturing techniques with microfluidic cell culturing using the same substrate material. Further, the attachment and detachment of the substrate simplifies pre- and post-processing steps which may have to be conducted at another location using conventional larger-scale equipment and which would necessitate the transport of the substrate to and from this other location. The use of a standard substrate, such as a glass or polystyrene microscope slide, makes pre- and post-processing steps much more convenient as the standard substrate can be used directly with conventional larger-scale equipment such as a microscope or plate reader. In one embodiment, the device can be used directly with a microscope so that it is not necessary to detach the substrate to view the biological material attached thereto. This could be done by making the device from transparent material.

The device may include an interconnect system having a first component having a conduit there through to carry fluid to the fluid inlet or away from the fluid outlet, wherein the first component is formed of a deformable material, and a second component having a projecting portion, wherein a conduit passes through the projecting portion and the second component. In some embodiments, the conduit of the first component is aligned with the conduit of the second component, and the projecting portion of the second component deforms an area of the first component surrounding the conduit therein so as to create a seal around the contiguous conduits of the first and second components, thus inhibiting and/or preventing any fluid from escaping as it flows from one conduit to the other conduit, and wherein the second component is for connecting the conduit therein to an external fluid source or sink.

Preferably, the device comprises an interconnect system for each of the fluid inlet and fluid outlet.

The advantage of such an interconnect system is that it allows the device to be easily and robustly connected to external fluid sources in a leak-free manner. This vastly improves the macro-to-micro interface. The second component can easily be standardized to allow easy linkage with standard equipment, for example, 'robotized' liquid handling platforms.

The first component is made of a deformable material. This can be any suitable deformable material such as rubber or silicone (e.g. poly(dimethylsiloxane) (PDMS)). The material must be sufficiently deformable to allow the second component to deform it and create a seal therewith.

The second component is for connecting the conduit therein to an external fluid source or sink. This can be any suitable fluid source or sink and can be connected in any suitable way. Such connections are well known to those skilled in the art. For example, the second component can have a thread on the inside of the conduit to allow it to be connected to commonly available tubing connectors such as Upchurch finger tight units. This allows fluid from an external source to enter the device, pass through the chamber and exit the device. The second component can be made of any suit-able material. For example, the second component may be made of aluminum.

The projecting portion can be any suitable size or shape so that it can create a seal with the first member to allow fluid to pass from one conduit into the other conduit in a leak free manner. Preferably, the projecting portion is cylindrical in shape so that the conduit passes through the longitudinal axis of the cylinder. A cylindrical shape creates a better seal and it is easier to fabricate.

The conduit in the first and second components can be the same size or different sizes. The cross sectional area of the conduits may change along the length of the components. Preferably, the conduit of the first component has a cross sectional dimension of about 1 mm to about 2 mm. For example, the conduit may have a diameter of about 1 mm to about 2 mm and, more preferably, about 1.2 mm to about 1.4 mm.

Preferably, the interconnect system further comprises a guide positioned on the first component around the conduit therein and which mates with the projecting portion of the second component to align the conduit of the first component with the conduit of the second component. The advantage of the guide is that the two components are self aligning which makes it very easy to correctly connect the two components to align the conduits.

The guide may be any suitable guide for aligning the conduits of the two components. For example, the guide may comprise an opening which is substantially the same size and shape as the projecting portion of the second component so that the projecting portion slots into the guide in a similar manner to a plug and socket.

The microfluidic device may further comprise a heater, such as an electroheater like indium tin oxide, to allow the chamber and its contents to be heated to and maintained at a predetermined temperature. Therefore, when cells are being cultured in the chamber, the chamber can be kept at a suitable temperature rather than being kept in an incubator. Alternatively, the device may comprise a heater to heat the fluid before it reaches the fluid inlet so that fluid entering the chamber has been heated to a predetermined temperature. The heater may be integrated into the device. For example, the heater may be integrated into the substrate of the device in embodiments in which a substrate is present.

The device may further comprise immobilized optical sensors or biosensors. Such sensors, in particular, the optical sensors, could be integrated into the second component of the interconnect system provided they are made of a transparent thermoplastic polymers. The optical sensors or biosensors may be utilized for cell culture monitoring. In some embodiments, the optical sensors or biosensors may be introduced and configured with the disclosed lid.

The device may comprise a housing which contains the other elements or to which the other elements are attached. For example, in one embodiment, a microfluidic chip defines the chamber, the fluid inlets and outlets and any conduits connected to the fluid inlet and/or outlet. The housing contains the microfluidic chip and has suitable openings to allow access to the chamber for the sealable port and also to the conduits and/or fluid inlet and outlet. This housing can be a standard size and can accommodates the interconnect systems and the substrate. This can give a standard housing comprising all the necessary elements to provide the macro-to-micro interface for the microfluidic device. Customized microfluidic chips can then be placed in the standard housing according to the particular function of the device allowing easy connection to the sealable port, interconnect system, substrate, etc. In this respect, the housing should allow the device to be assembled and disassembled repeatedly. The housing may be made of any suitable material. For example, the housing may be made of aluminum. Alternatively, the housing may be made of a transparent material.

The present disclosure also provides an interconnect system for sealably connecting two fluid carrying conduits, the system comprising:

- a first component having a conduit therethrough and being formed of a deformable material; and
- a second component having a projecting portion, wherein a conduit passes through the projecting portion and the first component;
- wherein, in use, the conduit of the first component is aligned with the conduit of the second component and a force is applied to the second component so that the projecting portion deforms an area of the first component surrounding the conduit therein so as to create a seal around the contiguous conduits of the first and second components, thus preventing any fluid from escaping as it flows from one conduit to the other conduit.

Preferably, the interconnect system is for connecting a conduit in a microfluidic device to an external fluid carrying conduit.

Preferably, the interconnect system further comprises a guide positioned on the first component around the conduit therein and which mates with the projecting portion of the second component to align the conduit of the first component with the conduit of the second component.

Other features of the interconnect system may include those as described above.

The present disclosure also provides a microfluidic device comprising a chamber having a fluid inlet, a fluid outlet and a substrate for supporting biological material, the fluid inlet and the fluid outlet being positioned to direct fluid flowing from the fluid inlet to the fluid outlet through the chamber.

Other features of this device are as described above in relation to the device comprising the sealable port.

The present disclosure also provides a method of fabricating a microfluidic chip, the method comprising the steps of: a) forming a mold defining features of the microfluidic chip; b) pouring a curable polymer into the mold; c) curing the polymer to form a cured polymer sheet; d) releasing the cured polymer sheet from the mold; e) forming a membrane having a base layer and a overlying cured polymer layer; f) bonding the cured polymer sheet to the membrane; and g) removing the base layer of the membrane to release the microfluidic chip. The same curable polymer can be used in steps b) and e), and can be any suitable polymer such as silicone or polyurethane. Preferably the polymer is polydimethylsiloxane (PDMS). Preferably step a) is carried out by a milling process.

Advantageously, the PDMS in step b) is a 10:1 base to curing agent mixture. In this case, the PDMS is degassed prior to the pouring step. In a preferred embodiment, a covering sheet is clamped on top of the mold prior to the curing process. Preferably, the PDMS is cured in an oven at 80° C. for one hour.

Advantageously, the base layer of the membrane is a silanized silicon wafer and the overlying curable polymer layer is a PDMS layer. The PDMS layer may be spin coated on the silanized wafer at 500 rpm for 50 seconds to obtain a thickness of substantially 120 micrometers. Preferably, the membrane is cured in an oven at 80° C. for one hour.

Conveniently, the cured polymer is bonded to the membrane by plasma bonding.

In a preferred embodiment, a microfluidic chamber is formed in the microfluidic chip following step 7 depicted in FIG. 5.

Where the microfluidic device is used for culturing cells, for example, human embryonic stem cells (hESC), it can be used to study various properties of the cells under different medium perfusion conditions. For example, the impact of oxygen on expansion and differentiation of hESC can be determined. The use of the microfluidic device could also be integrated with post-process cell preparation.

Microfluidic cell culture systems, such as the present disclosure, operate with significantly fewer resources. They can also be parallelized so that multiple microfluidic devices can be combined into a single system. Further, the use of the disclosed microfluidic device can be automated. For example, automated pulse-free medium perfusion of cells can be performed by an automated system for execution of cell re-feed schedules. Alternatively, constant medium perfusion can be performed at different flow rates in a plurality of devices. This is applicable to execute fully-automated differentiation and expansion studies. Further, multiplexing of devices can be used for parallelized execution of cell-based assays.

Geometry-wise, conventional apparatus such as microfluidic bioreactors are differentiated from disclosed embodiments, because arrangements having conventional lid configurations do not provide adequate surface area that covers, for example, an entire bottom surface area of a culture chamber retaining the cells. Thus, some disclosed embodiments provide a lid structure that is appropriately dimensioned to be received in a sealed position within the chamber such that the lid structure is approximately the same as the inner dimensions of the side walls of the chamber. In some embodiments, the disclosed area of the lid is approximately the same area of the bottom of the chamber. In one select embodiment, the lid contains a protrusion which is configured to fill part of the volume of the chamber such that the chamber has a larger volume when the lid is in an open position. Thus, in a closed position, the lid may form the uppermost portion of the chamber thereby sealing the chamber. The lid may fill part of the volume of the chamber such that the chamber has a larger volume when the lid is in an open position. The cross sectional dimensions of the lid may be the same as the inner dimensions of the side walls of the chamber such that the lid is in contact with the side walls of the chamber when the lid is closed. Thus, the lid may match the footprint of the chamber. It is readily appreciated that particular angles and tapers of the lid architecture may be included in the design to match corresponding chamber architecture to allow the lid to form an appropriate seal with the chamber. The disclosed lid may not form an integral part of the top layer (or the uppermost portion) of the chamber of the microfluidic device. The disclosed lid may serve to seal the chamber and may form a separate structure that is independent from the rest of the disclosed device's architecture.

The lid may be made from any suitable deformable material such as rubber or silicone (e.g. poly(dimethylsiloxane) (PDMS)). Alternatively, the disclosed lid may be made of soft or hard materials including, for examples, gas-permeable and gas-impermeable materials. Thus, sealing of the disclosed chamber is independent of the selection of materials of the lid. The disclosed lid allows performing microfluidic operation as "open" microfluidics and "closed" microfluidics with the same disclosed microfluidic device. In select embodiments, the disclosed fluid channels may be filled with liquid with the disclosed lid in an open position or with the lid in a closed position. Furthermore, the fluid channels of the disclosed microfluidic device do not need to be emptied before the disclosed lid is removed from the substrate to access the cells of the disclosed chamber. The aforementioned eliminates any need, for example, as provided in conventional microfluidic devices, to force a gas through fluid channels to clear the same which could adversely affect the processed cells. In another disclosed embodiment, the lid may be configured to allow gas to enter the disclosed culture chamber if, for example, the lid comprises a gas-permeable material. Thus, in this instance, there is no need for the additional expense and added configuration to provide for an additional gas supply channel as required in some conventional systems.

The lid may be positioned at any location within the chamber. The device is operable when the lid is open or closed, and the lid can be opened or closed during use of the device, for example, during operation of microfluidics and/or perfusion operations of the device. The volume of the chamber is adjustable based on changing a dimension of the lid.

As previously mentioned, the lid may comprise a protrusion. In some disclosed embodiments, the sealable port may be positioned at any location within the culture chamber such as in alignment with the culture chamber. When the lid is closed, the protrusion of the lid may serve to mate with the opening of the sealable port to provide a hermetic seal. In doing so, the culture chamber is also closed off. Hence, in some disclosed embodiments, the uppermost portion of the culture chamber may be formed by the protrusion. Thus, in accordance with some disclosed embodiments, a microfluidic device is disclosed having a sealable port, wherein the lid has a protrusion that is closed to seal of the sealable port. In the closed position, the protrusion of the lid fills part of the volume of the culture chamber. The culture chamber has a larger volume such as when the lid is opened and the protrusion is removed from the sealable port thereby rendering the sealable port in an open position. The cross sectional dimensions of the protrusion of the lid may be configured as the same inner dimensions of the side walls of the chamber such that the protrusion is in contact with the side walls of the chamber when sealing the sealable port in a closed position. It is readily appreciated that the disclosed microfluidic device is operable when the sealable port is open or closed and wherein the sealable port can be opened or closed during use of the device, for example, during operation of microfluidics and/or perfusion operations of the device.

In accordance with disclosed embodiments, the sealable port provides multi-functionality to the culture chamber. For example, the chamber height of the culture chamber can be modulated using the length of the protrusion made, and this in turn modulates culture conditions, such as hydrodynamic shear stress, in the culture chamber (for the cells).

In on select embodiment, the disclosed protrusion of the lid covers the entire bottom surface area of the culture chamber retaining the cells. Thus a bottom area of the protrusion may correspond to approximately the entire bottom surface area of the culture chamber. The cross sectional dimensions of the protrusion of the lid may be the same as the inner dimensions of the side walls of the culture chamber. In an open position, unimpeded access to the entire culture chamber is provided such as when the protrusion is fully removed from sealing port.

The sealable port does not form an integral part of a top layer of the microfluidic device. Rather, the disclosed sealable port is a separate structure which offers additional functionality including effectively creating a dual-mode operable, multi-functional device. The sealable port is a separate structure entirely independent from the rest of the disclosed microfluidic device. Whereas, in some convention systems, a top layer typically covers the microfluidic device. In contrast, in the disclosed microfluidic device, there remains an additional lid/sealable port to open and close as a sub-section of the microfluidic device. The disclosed sealable port serves to seal the culture chamber and form a separate structure that is independent from the rest of the disclosed microfluidic device architecture. The disclosed sealable port provides a dual mode operable device, wherein the two modes are 'chamber open' ('open') and 'chamber closed' ('closed'). The remainder of the disclosed microfluidic device does not require to be manipulated or handled, let alone re-configured, in any way, in order to achieve the aforementioned duality.

In open mode, the disclosed microfluidic device can operate to insert and remove material. This includes, for example: loading: gels (ECM), single cell suspensions, cell colonies and clusters (including co-culture), beads, polymeric monoliths, etc. Removing operations may including Remove: gels (ECM) (including excess gel), single cell suspensions, cell colonies and clusters (including co-culture), beads, polymeric monoliths, etc. Cell harvesting does not require opening or destruction of the entire disclosed microfluidic device; cells can be removed destruction-free as they don't need to be flushed out. The disclosed microfluidic device may serve as a static culture device analogous to open-culture petri dishes (e.g., round or cuboidal). In addition, the disclosed microfluidic device may perform end-point cell assays, such as immunocytochemistry and operate as a continuous-flow closed-open-closed microfluidics device (e.g., Lab Chip, 2005, 5, 682-686). Notably the disclosed microfluidic device's fluidic channels can be filled in 'open' mode; the sealable port is a separate and completely independent structure from the rest of the device. Notably, the channels of the disclosed microfluidic device do not need to be emptied prior to removing the sealable port (e.g. to access the cells in the chamber); thus, there is no need to force a gas through channels of the disclosed microfluidic device which may adversely affect the cells as the channels do not need to be emptied to open the device; the sealable port is a separate and completely independent structure from the rest of the disclosed microfluidic device.

In closed mode, the disclosed microfluidic device can operate as a perfusion culture device (continuous or discrete perfusion) and/or as single culture or co-culture perfusion device. Additionally, the disclosed microfluidic device may employ enzymatic assays in flow and operate cell-based assays, such as cell:drug toxicology-tests.

Thus, the disclosed sealable port is multi-functional and provides multi-functionality to the culture chamber. There is no need to change the fluidic structures around the sealable port to attain the different functions, i.e., no need for a re-design of the disclosed microfluidic device. Only a slightly amended sealable port may be required, for example, to change characteristics of the disclosed culture chamber or operating conditions therein.

For example, with respect to the culture chamber height and modulation of shear stress, the larger the protrusion (thereby reducing the culture chamber height), the higher the hydrodynamic shear stress in the culture chamber for the exact same overall flow rate of the disclosed microfluidic device (vice versa, the shear stress can be modulated down).

With respect to the chamber material and modulation of oxygen provision, the disclosed sealable port can be made of different materials wherein, for example, a gas-permeable material provides additional oxygen, thus enhancing or lowering the oxygenation of the chamber via the functionality of the sealable port. Utilization of gas-impermeable materials may reduce oxygen provisions. Thus, the port may be made of soft or hard materials, both capable of sealing with the disclosed microfluidic device regardless of selected materials thanks, for example, due to the properties of the disclosed gasket's 4, 14 material selection.

With respect to the culture chamber height and oxygen and nutrient provision, the larger the disclosed protrusion 50 (reducing the culture chamber height), the shorter the diffusion distances (vertically), and thus the faster oxygen (from the top) and any molecules diffuse to the bottom of the culture chamber.

With respect to the culture chamber height and type of culture, the length of the disclosed protrusion may define the culture chamber height which can be made suitable, for example, to 2-dim and 3-dim cultures. 3-dim cultures having a third dimension vertical to the chamber surface.

In some disclosed embodiments, the sealable port is of same size as chamber, thus the sealable port does not impede monitoring of the chamber in any way. The sealable port, therefore, matches the footprint of the culture chamber. The rest of the disclosed microfluidic device remains completely assembled at all times, for example, for cell loading, medium perfusion, cell removal etc. The disclosed sealable port only opens (and closes) the culture chamber. In some disclosed embodiments, the disclosed sealable port is separate without fluidic interconnections, the fluidic interconnects being mounted on or part of a separate top layer of the disclosed microfluidic device. In an alternate embodiment, an extended architecture of the disclosed sealable port may be provided where specific fluidic connections are added onto the sealable port, which will have a different functionality than the other fluidic connections up- and down-stream of the disclosed culture chamber.

Hence, unlike conventional microfluidic device arrangements, disclosed embodiments provide a lid having a surface area that precisely fits within the opening of a chamber having side walls that correspond to the dimensions of the surface area of the lid. Thus, when the lid is inserted into the opening of the chamber, a tight friction fit is obtained to seal the chamber as the lid forms the uppermost portion of the chamber such that the lid is in contact with the side walls of the chamber when the lid is closed. As explained above, the lid may contain a protrusion which fits into the opening of the culture chamber. The protrusion may contain exterior walls which may be dimensioned to precisely fit into the corresponding interior walls of the culture chamber as the protrusion is inserted into the opening thereof to form a tight interference fit.

Thus, when the disclosed lid is removed the interior walls and bottom of the culture chamber may be fully exposed and accessible, such as for cell seeding. Thus, no obstacles or interferences are disposed within the culture chamber to prevent full cell seeding, for example, across all portions of the culture chamber bottom and along and at the intersection of the culture chamber bottom and culture chamber interior walls. This critical aspect remains important for performing proper static cell seeding and achieving proper fluid overlay in the culture chamber. Thus, closing the culture chamber with the disclosed lid provides a multifunctional dual mode device also capable of performing microfluidics within the same device.

The importance of the disclosed lid surface area covering the entire surface area of the disclosed culture chamber allows full access (i.e., unimpeded access) to the bottom of the disclosed culture chamber. Thus, when the cells are brought in or introduced into the culture chamber, for example, using a fine pipette technique, a technician can put the cells all across the entire surface area of the bottom of the culture chamber—i.e., the technician does not have to worry about traversing around any corners. During this feeding stage, a technician can have a culture medium that is fitting about the cells. In addition, the top surface of the liquid layer may provide the gas exchange thereby providing a direct contact to air. This surface area will match the surface area of the culture chamber area where the cells sit below. Thus, disclosed embodiments effectively mimic (such as during the static seeding step) a scenario where one would have in any tissue culture vessel. In an additional embodiment, removable structure designed for cell seeding may be employed, for example, to increase the height of the fluidic overlay during cell seeding.

In one exemplary embodiment, the culture chamber 11 footprint may be approximately 4 mm×13 mm. The height of culture chamber 11 when closed with lid 1 may be approximately 0.45 mm (i.e. about half mm). The height of culture chamber 11 may be increased, for example, by reducing the protrusion 50 leg of the T-piece shaped lid 1. When the disclosed microfluidic device is open, the culture medium overlay may be approximately 2-3 mm. The volume and/or thickness of the aforementioned medium overly may be increased, for example, by increasing the thickness of the top plate 3.

In a conventional petri dish, cells may be spread on the bottom of a petri dish, with a culture medium on top of them (such as a cultural fluid overlay of about 2 mm (or about 1.5-4 mm)). The cells may receive nutrients from the culture medium. An amount of liquid above the cells in the cultural fluid overlay may provide a nutrient reservoir. The nutrients may be depleted by the consumption from the cells. In turn, the cells may secrete some waste. The lower the culture fluid overlay is, the less nutrients there are; and the more waste product from the cells builds up per volume, hence producing more contamination. Without the proper cultural fluid overlay, there exist the possibility of having too quick of an evaporation thereby leaving the cells dried out after a few hours.

It is relevant that although the disclosed invention may include a relatively shallow microfluidic device (planar) for receiving cells introduced thereto, disclosed structural elements of the disclosed embodiments may mimic the static culture step occurring, for example in a flask wherein: cells may be diluted in a culture medium and introduced into a pipette into a flask; the cells within the medium within the flask float; the cells settle and may attach and spread on the floor (or bottom) of the flask and the culture begins. However, an improvement over convention apparatus by the disclosed invention includes the capability to provide multifunctional tasks/operations within the same device. According to the present disclosure, when the cell culture is matured and ready for further processing, the disclosed lid may be assembled to the culture chamber and/or closed whereupon a microfluidic process may be enacted directly by the same disclosed device—i.e., utilizing the microfluidic cell culture device of the disclosed invention to perfuse the culture medium wherein the fluid flow is used to bring nutrients to the cells and remove waste product from the cells. Multifunctional features to provide cell seeding and microfluidic procedures is not known to be achieved within a singular conventional apparatus (e.g., a flask device). The functionality of conventional equipment is therefore limited in its purpose and/or design for merely providing a singular static culture capability without additional inclusive functionality such as performing or having microfluidics capability in contrast to disclosed embodiments which provide capability for various operation modes such as (micro) perfusion (continuous, discrete) etc. Accordingly, conventional apparatus, such as a flask device, is limited in that it may only provide static culture capability and not a microfluidics function as disclosed herein by the present disclosure.

Turning again to the discussion of cell seeding within a conventional petri dish, the oxygen demand for the cells may be provided via the air above the fluid overlay through the liquid to the cells. In a petri dish, normally all of the culture liquid area remains in direct contact with the air above. If only half of the area were in contact, for example, in a round 2-inch diameter petri dish, the fluid/liquid would for example only be in contact with air within the diameter of 1 inch in the center (and not the outer ½ inch diameter of the petri dish). Thus, any cells within the outer ½ inch diameter of the petri dish would not receive the same amount of oxygen as the cells within the center 1 inch diameter of the petri dish. Thus, a proper static culture could not be obtained. Accordingly, if the disclosed embodiments did not provide for a lid to allow for opening the culture chamber entirely, then a proper static culture could not be obtained. However, because disclosed embodiments do provide removing the lid and do provide complete exposure of the culture chamber, proper static culture may indeed be obtained. In fact, during the static feeding/static culturing step, which can last over a variety of time (e.g., 6 hours or 24 hours), present embodiments may provide a culture fluid overlay of 2 mm, thereby mimicking what one would obtain in a petri dish (or flask).

Disclosed embodiments provide the ability through features of the disclosed device for closing the culture chamber such as via the disclosed lid. In this manner a microfluidic culture scenario is achieved which may include a shallow culture fluid overlay in perfusion. The disclosed lid may be provided as a smart-type lid which is utilized to cleverly and uniquely switch between at least two modes of operation of the disclosed device to perform operations of microfluidics and/or perfusion depending, for example, upon operating conditions and a disclosed set-up. Thus, disclosed embodiments provide a microfluidic device that switches between at least two modes of operation to thereby provide a dual embodiment or configuration. The enhanced feature of the enablement and/or disablement of the unique configuration and use of the disclosed lid is enabled through its engagement or disengagement with the microfluidic device.

Thus, contrary to the disclosed invention, conventional apparatus for microfluidic devices cannot provide both proper static seeding (cell seeding) and microfluidics (perfusion) all within the same microfluidic device. Many conventional devices for performing microfluidics may include microfluidic cell culture devices for perfusing culture medium to utilize the fluid flow to bring nutrients to the cells and remove waste product from the cells. However, disclosed embodiments of the disclosed invention provide an enhanced microfluidic device that may also be regarded as an enhanced microperfusion device with capability for both static seeding and culture and also for culture perfusion. The microfluidic, per se, as a physics of this disclosed scale gives very precise control over the fluid flow which is not obtainable at a larger scale, hence the unique attraction of performing this procedure at a small scale. The disclosed process and embodiment yields better control over the amount of nutrients and positioning the nutrients to provide an enhanced better controlled ultra-mode design.

Advantages provided by disclosed embodiments include not only the capability to culture cells in any possible way due to the full accessibility of the culture chamber but provide for applications in enzymatic assays and biofilm implementations. The disclosed microfluidic device may begin processes without any modification and is not regarded as single use unlike conventional designs which typically may require a need to destruct a chip in order to reuse; notably, systems requiring a membrane, cells cannot be removed properly from a porous membrane. Disclosed embodiments may lift off the ceiling of the culture chamber and use it to add material. In disclosed embodiments, the geometry of the culture chamber is not limited (for example to round and/or small diameters) and is completely unconstructively accessible. Thus, in the design of the accessibility and of the disclosed culture chamber, cells are on TC-PS or any cell growth material to the bottom, fluid structures to the side, and ceiling that may be mounted or dismounted at will. No fluidic port resides over a porous member such as a cellulose acetate membrane as in some conventional systems. Accordingly, no extra microactuator/valve is necessary to operate to operate the addition or removal of material (e.g., cells, extracellular matrices, etc.) nor is any flow reversal to remove the cells from the culture chamber required. For select applications where cross-contamination is not an issue (e.g., such as for enzyme-based assays), the design of the disclosed device allows for easy re-use of the device.

Conventional designs may also require pressure to remove cells from the culture chamber. This process can create a cell viability issue. Alternatively, present embodiments of the disclosed invention allow for access to cells with a pipette and to clean without residues. The disclosed culture chamber is accessible such that a pipette or automated system may be employed. Disclosed embodiments provide a configuration wherein oxygen or carbon dioxide feed the cells. Disclosed embodiments do not pressure the cells and reduce/eliminate cake formation over time thereby reducing/eliminating a risk of foul cells which may kill good cells. A design of the disclosed embodiment provides a lid that has an equilibrium function for cells that is therefore an integral part of the culture chamber.

The disclosed lid can allow access to remove everything from the culture chamber in a bubble-free environment. The disclosed device may be cleaned indestructibly. In contrast, some conventional microfluidic systems do not provide a functioning cell culture and cells cannot be removed indestructibly. Within such conventional microfluidic systems, the membrane is not exchangeable and is merely single use. Furthermore, conventional microfluidic systems typically destruct their chip to reuse. Even more, typical microfluidic systems do not optically read-out as a membrane is not optically transparent (it is a woven structure); therefore some typical microfluidic systems do not provide a culture chamber as disclosed by present embodiments. Furthermore, the membrane of conventional microfluidic systems, in contrast to disclosed embodiments, is not controllable. Thus, controlled cell culture is not possible in conventional microfluidic systems, for example, due to clogs and closures in the membrane. This contributes to added pressure build-up in conventional systems when fluidic operations are employed for flushing the system or obtaining cells. These and other advantages of the disclosed design including the interconnect system which allows easy, self-aligning interfacing (macro- with micro-environment) of microfluidic PDMS devices provide enhanced microfluidics and perfusion techniques over conventional designs.

Disclosed aspects of the invention provide a unique interface/interconnect system for the disclosed deformable microfluidic chip. Such an interface/interconnect system may include fluidic inlets and outlets of a microfluidic chip, but also provide a direct access port to the central functional feature of the disclosed microfluidic device. Some embodiments may entail a direct access port connecting with a microfluidic layer, for example, underneath the top layer of the interface/interconnect system wherein such a microfluidic layer may be considered to be one of a deformable material, a weakly deformable material, or a non-deformable material. Such a central functional feature may be considered as the culture chamber in the embodiment of a disclosed cell culture device (with or without a deformable chip). In addition, present techniques consider an interface/interconnect system for a microfluidic chip of microfluidic material wherein such an interface/interconnect system may be used with a deformable chip. The disclosed culture device comprising the capability to provide facility to open and close the central feature of the culture chamber independently from employed fluidic ports with all other parts remaining assembled.

In some embodiments, a microfluidic device may include an interconnect system having a first component which includes a conduit to carry fluid to the fluid inlet or away from the fluid outlet. Some embodiments may include a first component formed of a deformable material. Some embodiments of a microfluidic device may include a second component having a projecting portion. In some embodiments, a conduit passes through the projecting portion and the second component. The conduits of the first and second components may be aligned. wherein the projecting portion of the second component deforms an area of the first component surrounding the conduit therein so as to create a seal around the contiguous conduits of the first and second components, thus preventing any fluid from escaping as it flows from one conduit to the other conduit, and wherein the second component is for connecting the conduit therein to an external fluid source or sink.

Some embodiments may include an interconnect system for each of the fluid inlet and fluid outlet. In various embodiments, the interconnect system or systems may include a guide positioned around the conduit on the first component and may mate with the projecting portion of the second component to align the conduits of the first and second components.

In some embodiments, the base of the chamber of a microfluidic device is formed from a substrate for supporting biological material. Some embodiments of substrates may include, but are not limited to glass (e.g., glass slide), plastic or polymer (e.g., polystyrene microscopy slide), culture plate and/or any material known in the art. The chamber may be formed on at least a portion of the substrate. In some embodiments, the substrate may be detachable from the device.

Embodiments of the microfluidic device may be used for culturing cells. In various embodiments, the device may be used for culturing cells and/or performing cell-based assays. Some embodiments may include a housing.

In some embodiments, the fluid inlet and the fluid outlet may be positioned on opposite sides of the chamber. Various embodiments include a fluid inlet and a fluid outlet which are positioned so that a material containment portion of the chamber is substantially unaffected by the flow of fluid through the chamber. In some embodiments, the fluid inlet and/or the fluid outlet each form at least about 20% of the area of one side of the chamber. Embodiments may include a fluid inlet and/or fluid outlet aligned with the top of the chamber. In some embodiments, the fluid inlet and fluid outlet may include one or more flow restrictors.

Embodiments may include a conduit to carry fluid to the fluid inlet and a conduit to carry fluid away from the fluid outlet. Conduits may include one or more flow dividers.

In some embodiments, the lid may be employed to seal a sealable port of the chamber. Some embodiments may include a liquid as the fluid. In various embodiments, the sealable port may include a gas permeable membrane to allow gas such as oxygen to pass into the chamber.

In some embodiments, the microfluidic device may include a heater and/or sensor.

In some embodiments an interconnect system for sealably connecting two fluid carrying conduits may include a first component having a conduit formed of a deformable material; and a second component having a projecting portion having a conduit which passes through the projecting portion and the first component. In various embodiments, during use, the conduit of the first component is aligned with the conduit of the second component. In some embodiments, when force is applied to the second component the projecting portion deforms an area of the first component surrounding the conduit to create a seal around the contiguous conduits of the first and second components, thus inhibiting and/or preventing any fluid from escaping as it flows from one conduit to the other conduit.

Some embodiments may include an interconnect system configurable to connect and/or connecting a conduit in a microfluidic device to an external fluid carrying conduit.

In some embodiments, the interconnect system may include a guide positioned on the first component around the conduit therein and which mates with the projecting portion of the second component to align the conduit of the first component with the conduit of the second component.

Some embodiments of a microfluidic device may include a chamber having a fluid inlet, a fluid outlet and a substrate for supporting biological material, the fluid inlet and the fluid outlet being positioned to direct fluid flowing from the fluid inlet to the fluid outlet through the chamber. In some embodiments, the substrate forms the base of the chamber of the microfluidic device. Some embodiments of substrates may include, but are not limited to glass (e.g., glass slide), plastic or polymer (e.g., polystyrene microscopy slide), culture plate and/or any material known in the art. The chamber may be formed on at least a portion of the substrate. In some embodiments, the substrate may be detachable from the device.

In some embodiments, a microfluidic device may include an interconnect system having a first component with a conduit to carry fluid to the fluid inlet or away from the fluid outlet. Some embodiments may include a first component formed of a deformable material. Various embodiments may include a second component having a projecting portion and a conduit passing through the projecting portion and the second component. In some embodiments, the conduit of the first component may be aligned with the conduit of the second component, and the projecting portion of the second component may deform an area of the first component surrounding the conduit to create a seal around the contiguous conduits of the first and second components, thus inhibiting and/or preventing any fluid from escaping as it flows from one conduit to the other conduit. In some embodiments, the second component may be used to connect the conduit therein to an external fluid source or sink. The microfluidic device may include an interconnect system for each of the fluid inlet and fluid outlet. Some embodiments may include one or more interconnect systems having a guide positioned on the first component around the conduit which mates with the projecting portion of the second component to align the conduits of the first and components.

In some embodiments, a method of fabricating a microfluidic chip may include forming a mold defining features of the microfluidic chip; pouring a curable polymer into the mold; curing the polymer to form a cured polymer sheet; releasing the cured polymer sheet from the mold; forming a membrane wherein, in some embodiments, the membrane may include having a base layer and a overlying cured polymer layer; bonding the cured polymer sheet to the membrane; and removing the base layer of the membrane to release the microfluidic chip. Some embodiments may utilize the same curable polymer for pouring the curable polymer into the mold and overlying a cured polymer layer. In various embodiments, the polymer is polydimethylsiloxane (PDMS). Some embodiments may include forming a mold defining features of the microfluidic chip using a milling process. In some embodiments, the PDMS used in pouring polymer into the mold is used in a 10:1 base to curing agent mixture. Some embodiments include clamping a covering sheet on top of the mold prior to the curing process.

In some embodiments, the base layer of the membrane is a silanized silicon wafer and the overlying curable polymer layer is a PDMS layer. Various embodiments may include spin coating the PDMS layer on the silanized wafer at 500 rpm for 50 seconds. In some embodiments, the spin coated PDMS layer may include a working range thickness of approximately 0-1 micrometers. A preferred range may include approximately 50-300 micrometers.

In some embodiments, the cured polymer is bonded to the membrane by plasma bonding. In various embodiment, after removing the base layer of the membrane to release the microfluidic chip, a microfluidic chamber is formed in the microfluidic chip. In some embodiments, the PDMS is cured in an oven at about 80° C. for about one hour.

In some embodiments, a microfluidic device for culturing cells comprises: a chamber having a fluid inlet and a fluid outlet; and a lid, wherein the fluid inlet and the fluid outlet are positioned to direct fluid flowing from the fluid inlet to the fluid outlet through the chamber, and wherein the lid is aligned with the chamber to allow cells to be placed directly into, or removed from, the chamber from the exterior of the device when the lid is open, and to prevent fluid escaping through the port when the lid is sealed, wherein the lid fills part of the volume of the chamber such that the chamber has a larger volume when the lid is in an open position, wherein the cross sectional dimensions of the lid are the same as the inner dimensions of the side walls of the chamber such that the lid is in contact with the side walls of the chamber when the lid is closed, wherein the device is operable when the lid is open or closed, and wherein the lid can be opened or closed during use of the device.

In some embodiments, a microfluidic device for culturing cells comprises: a chamber having a fluid inlet and a fluid outlet; and a sealable port, wherein the fluid inlet and the fluid outlet are positioned to direct fluid flowing from the fluid inlet to the fluid outlet through the chamber, and wherein the sealable port is aligned with the chamber to allow cells to be placed directly into, or removed from, the chamber from the exterior of the device when the sealable port is open, and to prevent fluid escaping through the sealable port when the port is sealed, wherein the lid has a protrusion which fills part of the volume of the chamber such that the chamber has a larger volume when the sealable port is in an open position, wherein the cross sectional dimensions of the protrusion of the lid are the same as the inner dimensions of the side walls of the chamber such that the protrusion is in contact with the side walls of the chamber when the sealable port is closed, wherein the device is operable when the sealable port is open or closed, and wherein the sealable port can be opened or closed during use of the device.

In some embodiments, a method of using a microfluidic device comprises: culturing cells and/or performing cell-based or enzymatic assays.

In some embodiments, a method of treating cell cultures in a microfluidic device comprises: configuring the device to culture cells; culturing the cells; configuring the device to perform cell-based or enzymatic assays within the same device; and performing cell-based or enzymatic assays.

In some embodiments, a method of using a microfluidic device comprises seeding cells in the device when the sealable port is open; and perfusing the cells when the sealable port is closed.

In some embodiments, a method of treating cell cultures in a microfluidic device comprises: configuring the device to seed cells in the device; seeding cells in the device; configuring the device to perfuse cells in the same device; and perfusing the cells.

In some embodiments, a multifunctional dual mode microfluidic device comprises: a first operating configuration; and a second operating configuration, wherein in the first operating configuration, the device is configured to perform static cell seeding, wherein in the second operating configuration, the device is configured to perform perfusion via microfluidics of the device, wherein the device is configured to switch between the first operating configuration and the second operating configuration.

In some embodiments, a multifunctional dual mode microfluidic device configured to selectively switch between two modes of operation comprises: a first operating configuration; and a second operating configuration, wherein the first operating configuration comprises an open chamber having a fluid inlet and a fluid outlet, wherein the fluid inlet and the fluid outlet are positioned to direct fluid flowing from the fluid inlet to the fluid outlet through the chamber, and wherein chamber is configured to allow cells to be placed directly into, or removed from, the chamber from the exterior of the device, wherein the second operating configuration comprises a sealable port aligned and sealed with the chamber to prevent fluid escaping through the sealable port in a closed position, wherein the lid has a protrusion which fills part of the volume of the chamber, wherein the cross sectional dimensions of the protrusion of the lid are the same as the inner dimensions of the side walls of the chamber such that the protrusion is in contact with the side walls of the chamber in a closed position, and wherein the device is configured to switch between the first operating configuration and the second operating configuration.

The present disclosure will be further illustrated in the following Examples which are given for illustration purposes only and are not intended to limit the invention in any way.

EXAMPLES

Example 1

Design of a Microfluidic Perfusion Bioreactor

As shown in FIG. 1A, to integrate a tissue culture polystyrene slide 6, a standard adherent cell culture material, into a microfluidic perfusion bioreactor, a clamp designed with integrated fluidic interconnects 2 was proposed, where a cell culture slide 6 and a microfluidic chip 5 were disposed between a bottom frame 7 and a top plate 3.

The clamp was held together by screws, where the soft microfluidic chip formed a seal between the culture slide and the interconnects in the top plate. In some embodiments, any fastening mechanism known in the art may be used to hold the MPB together. As shown in FIG. 1A, the top plate 3 included two pockets to hold the gasket 4 and the microfluidic chip 5 and which allowed alignment of the microfluidic chip with the inlet and outlet interconnects 2. Interconnects 2 may be mounted on the top plate 3 with screws and a portion of the interconnects extend through a hole in the top plate 3. A projection 20 (shown in FIG. 3) at the bottom of the interconnect was pressed against the microfluidic chip and formed a tight seal 8' (shown as dotted circle in FIG. 1B) around the inlet and outlet port 8 (shown in FIG. 1B), when the MPB was assembled. (shown in FIG. 3)

The projection stood out approximately 80 μm into the microfluidic chip pocket from the top plate to assure that the cylinder is pressed reliably against the microfluidic chip, when clamped.

The interconnects had on the top side a thread, which allowed the use of commonly available tubing connectors, (such as Upchurch fingertight units).

An alternative embodiment of the disclosed interconnect is shown in FIG. 4. In this embodiment the projection 23 is on the top plate 24 of the MPB rather than on the interconnect itself. The interconnect 26 is mounted on the top plate and a seal is formed between the top plate and interconnect using a rubberized O-ring 25. Alternatively, the interconnect can be formed integrally with the top plate to allow fabrication of the top plate and interconnect in one piece.

The disclosed interconnects may be made of aluminum, thermoplastic polymer and/or other materials known in the art. In some embodiments, aluminum is preferred.

To avoid dissociation of hESC colonies during seeding into the microfluidic perfusion bioreactor, a sealable lid was designed, enabling two configurations of the MPB. When the lid is not mounted, the MPB is in a cell seeding configuration. When the lid is mounted, the MPB is in a perfusion configuration. This allows co-culture seeding and perfusion of hESC on a feeder layer and the use of a pipette for simple and accurate seeding into the MPB (defined colony numbers, cell density).

As depicted in FIG. 1A, a gasket 4 made out of PDMS was incorporated into the design to guarantee a leak-age free closing of the MPB after seeding. When the MPB was in seeding configuration, the height of the gasket and the microfluidic chip allowed the same surface area to volume ("SAY") ratio as in a one well dish or a T-flask.

After successful seeding and attachment of the cells, the lid 1 (shown in FIG. 1A) could be screwed onto the top plate 3 to close the MPB. The lid 1 determines the chamber height in the culture chamber during perfusion. In one embodiment, this is about 500 μm (shown in FIG. 1C, upper solid line). This leads to a total volume of about 4 mm×13 mm×0.5 mm=26 microlitres.

As shown in FIG. 1A, this device enables the use of disposable polymeric microfluidic chips 5 which can easily be redesigned and inserted into the standardized housing.

As depicted in FIGS. 1B-C, in some embodiments, the microfluidic chip 5 had nineteen flow restrictors 10 on each side of the culture chamber. In various embodiments, the flow restrictors may have dimensions of about 200 μm wide and about 1000 μm long. In some embodiments, channels between the restrictors were about 400 μm wide and about 200 μm high. As shown in FIG. 1*b*, the inlet 8 was divided into three channels acting as a microfluidic manifold 9 to create together with the flow restrictors 10 an even velocity pattern in the culture area and therefore an even distribution of shear stress within the culture chamber (in flow direction, y-direction).

As shown in FIG. 1C, a layer (shown between lower solid and dashed line) at the bottom of the microfluidic chip elevated the height of the flow restrictors to above the cell culture portion of the chamber (in between the solid line and dashed line at the bottom of the chamber of FIG. 1C), reducing the flow rate and the hydrodynamic shear stress on the cell culture. FIG. 2 depicts the layer as membrane 19.

As shown in FIG. 1B, to accommodate hESC colonies sized up to 1 mm in diameter, an appropriate sized culture chamber body 11 was incorporated. In one embodiment of an MPB, the cell culture area had a size of 0.52 $cm^2$.

FIG. 1A depicts bottom frame 7 had a recess incorporated to hold different microscope slide formats. The bot-tom frame was reinforced underneath the sealing area to avoid excessive bending of the bottom frame when clamped together. An opening under the culture chamber area allowed access for inverted microscopes. The bottom frame was fitted with threads to screw together with the top plate.

Example 2

Fabrication and Assembly of the Microfluidic Bioreactor

All parts and molds were designed in a 3D CAD system (SolidWorks 2007, Dassault Systemes SolidWorks, USA). G-code was generated with a CAM program (Master-Cam X2, CNC Software, USA) to control the milling process on a micro milling machine (M3400E, Folken Industries, USA).

To mill the bottom frame 7 and top plate 3 (shown in FIG. 1A), a 3 mm thick poly(carbonate) (PC) sheet (681-637, RS, UK) was machined (8,000 rpm, 104 mm min-1 feedrate) using 2 mm diameter end mills (2 flute standard length, Kyocera Micro Tools, USA). The lid 1 as depicted in FIG. 1A was machined from a 5 mm thick PC sheet (681-659, RS, UK) using 2 mm diameter and 1 mm diameter end mills (2 flute standard length, Kyocera Micro Tools, USA).

Instead of using a SU-8 process, which creates a master for PDMS reproduction, the inventors used a micromilling machine to fabricate molds for the microfluidic chip (FIG. 5) and the gasket.

As shown in FIG. 5, in steps 1 and 2 the mold 32 for the microfluidic manifold layer was milled 28 (8,000-16,000 rpm, 104 mm min-1) in Dural with 2 mm, 1 mm and 200 μm diameter end mills (2 flute standard length, Kyocera Micro Tools, USA). 2 mm and 1 mm diameter end mills were used to create microfluidic manifolds or channels. A 200 μm diameter end mill was used to machine the flow restrictors.

Poly(dimethylsiloxane) (PDMS) (Sylgard 184, Dow Corning, USA) was mixed in a ratio of 10:1, base to curing agent, and degassed for 15 minutes. As shown in step 3 of FIG. 5, the PDMS was poured into the negative Dural mold and thoroughly degassed again until no air bubbles were visible. A 3 mm thick PC sheet was then placed carefully on top of the mold as shown in step 4 of FIG. 5 and clamped between two aluminum plates. The clamped stack was placed in an oven at 80° C. for 1 hour to cure the PDMS.

After releasing the mold/PC sheet stack from the clamping plates, the mold together with the polycarbonate sheet was left to cool. The microfluidic manifold layer was then freed from the mold with tweezers as shown in FIG. 5, step 5. The culture chamber body of the microfluidic manifold layer was cut out with a scalpel under a microscope.

As depicted in FIG. 1C, the thickness of a PDMS membrane defined the height of the flow restrictors above the culture chamber (shown as the height between the solid and the dashed line).

First, a 4" silicon wafer (100, P-type, Prolog Semi-cor, Ukraine) was silanized (85041C, Sigma-Aldrich, UK) to prevent subsequent sticking of the PDMS. 200 μl of the trichlorosilane was pipetted into a vial and placed with the silicon wafer in a desiccator for 1 hour.

5 ml of degassed PDMS was spun with a spin coater (P6708D, Specialty Coating Systems, USA) on the silanized wafer at 500 rpm for 50 seconds to obtain a thickness of approximately 120 μm and placed in an oven at 80° C. for 1 hour.

To bond the thin PDMS membrane 34 with the PDMS microfluidic manifold layer 33, an air plasma was used. Before bonding, the PDMS-coated wafer and the microfluidic manifold layer were rinsed with ethanol and subsequently dried. Both PDMS layers were then exposed to air plasma for 90 seconds at 30 Wand 500 mTorr (PDC-002, Barrick Plasma, USA). As shown in step 6 of FIG. 5, the microfluidic manifold layer and the membrane on the wafer were then immediately brought into contact for bonding. To further strengthen the bond, the microfluidic chip 38 was placed in an oven at 80° C. for at least 2 hours.

Step 7 of FIG. 5 depicts cutting the culture chamber body. To provide access to the culture slide, the culture chamber body had to be cut out of the membrane with a scalpel. The microfluidic chip was cut out after and gently released from the silicon wafer with a tweezer.

The interconnect was made of an aluminum block. A thread was cut into the top for an Upchurch fingertight unit. The bottom of the interconnect had a 2.08 mm high cylinder (6 mm in diameter) to form a seal as previously described.

The dimensions of the mold and the microfluidic chip were measured with a stylus profilometer (Dektak 8, Veeco Instruments Company, USA) and the quality of the mold was inspected with a SEM (XB1540 "Cross-Beam", Carl Zeiss AG, Germany).

Prior to assembly, all parts of the MPB were autoclaved, except the cell culture slide. Assembly of the MPB was carried out in a sterile hood.

A sterile tissue culture polystyrene slide (16004, Nurre, Denmark) was placed in the bottom frame. The gasket was placed into the top plate first, followed by the microfluidic chip. The top plate with the microfluidic chip was then carefully placed over the bottom frame with the culture slide and held in place with gently tightened screws, sealing the entire device.

Example 3

Cell Culture Maintenance

Primary murine embryonic fibroblasts (MEF) were maintained in Dulbecco's Modified Eagle Medium (DMEM) (41965, Invitrogen, USA) supplemented with sodium pyruvate (11360, Invitrogen, USA), 10% (v/v) heat inactivated foetal bovine serum (FBS) (10270, Invitrogen, USA) and 1% (v/v) Modified Eagle Medium Non-Essential Amino Acids (MEM NEAA) (11140, Invitrogen, USA) and passaged every 3 days into T75 flasks (159910, Nurre, Denmark) in a humidified environment at 37° C. with 5% CO2.

To inactivate MEFs, the T75 flasks were aspirated and replaced with mitomycin C.

DMEM (11960, Invitrogen, USA) was supplemented with 10% (v/v) FBS (10808, Invitrogen, USA), 1% (v/v) MEMNEAA (11140, Invitrogen, USA) and 8 mgmL-1 mitomycin C (M4287, Sigma-Aldrich, UK) and filtered. 5 mL of mitomycin C solution was added to a T75 flask and incubated for 2 hours at 37° C. The flask was then aspirated and washed with Dulbecco's phosphate buffer solution (DPBS) (D1408, Sigma-Aldrich, UK) three times. Inactivated MEFs were then trypsinized with trypsin:EDTA (T4049, Sigma-Aldrich, UK) and incubated for 3 minutes. The suspension was spun down and the supernatant resus-pended. T25 flasks (156367, Nurre, Denmark) were incubated with a 0.1% (v/v) in DPBS gelatine solution (G1890, Sigma-Aldrich, UK) for 10 minutes at room temperature. The flasks were aspirated and filled with 15,000 cells cm-2.

In experiments, the inventors used the Shef-3 cell line obtained from the UK Stem Cell Bank. Use of the line was approved by the UK Steering Committee.

Human ESC (hESC) (Shef-3) were cultivated on a mitomycin-c inactivated feeder layer of primary MEFs (MEFs<passage 5) in T25 flasks (156367, Nurre, Denmark) as stock with filtered KnockOut DMEM (10829, Invitrogen, USA) and KnockOut Serum Replacement (10828, Invitrogen, USA) and supplemented with MEM NEAA (11140, Invitrogen, USA), L-Glutamin (21051, Invitrogen, USA), mercaptoethanol (M3148, Sigma-Aldrich, UK) and FGF2 (4114-TC, R & D Systems, USA).

hESC were passaged in small clumps every 3 days using collagenase IV (17104, Invitrogen, USA).

The flasks were incubated with collagenase for 3-5 minutes, before hESC colonies were scraped off the flask surface and replated on a MEF feeder layer.

Example 4

Seeding and Experimental Procedure

The lid of a 150 mm diameter glass Petri dish (2175553, Schott, USA) was fitted with three custom made silicone spacers to enhance gas exchange in an incubator. These Petri dishes were used to provide a sterile environment for the MPB in seeding configuration (FIG. 6).

Prior to seeding, the Petri dishes, pipette tips and tubing to be used were autoclaved and dried.

On day 0, 200 μL of 0.1% (v/v) gelatine in DPBS solution was added into the cell culture area of the MPB and incubated for 10 minutes at room temperature in a sterile laminar flow hood. The gelatine was then aspirated and the MPB was left to dry for 30 minutes. 20,000 inactivated MEFs were seeded into the cell culture area of the MPB (shown in FIG. 6, step 1). The customized lid was put on the Petri dish, which accommodated the MPB, and placed in an incubator (FIG. 6, step 2).

To compare the MPB with traditional static tissue culture methods, three one well dishes (353652, BD Bio-sciences, USA) were incubated with 0.1% (v/v) gelatine in DPBS solution (G1890, Sigma-Aldrich, UK) for 10 minutes, aspirated and then seeded with 40,000 inactivated MEFs per one well dish.

Inactivated MEFs were counted with a haemacytometer (0630030, Marienfeld, Germany).

Before seeding with hESC colonies on day 1, the one well dishes and the MPB were aspirated and replaced with new hESC medium at least 30 minutes before transferring hESC colonies.

When hESC colonies were routinely passaged in the stock flask, the colonies in medium were transferred into the one well dishes. A drop with hESC colonies in a small Petri dish (Nurre, Denmark) was used to transfer colonies for the MPBs. hESC colonies in the small Petri dish were caught with a 10 μL pipette and then transferred gently to the culture area in the MPB (FIG. 6, step 3) and the Petri dish was closed again (FIG. 6, step 4). One well dishes and MPB were then incubated overnight at 37° C. in an incubator to allow attach-ment of the hESC colonies to the feeder layer.

On day 2, the hESC colonies had spread and attached to the feeder layer. The medium in the control dishes was replaced every 24 hours for the entire time of the experiment. Medium in the MPB was aspirated, the lid for the MPB put on, tubing for medium and the waste were connected and continuous perfusion was started for 48 hours and was stopped on day 4 of the experiment (FIG. 6, step 5).

The perfusion system consists of a syringe pump (Model 100, KD Scientific, USA), silastic tubing (R3607, Tygon, USA) with Luer adapters (Cole-Palmer, USA), autoclavable tubing (R1230, Upchurch Scientific, USA) with fit-tings for the custom interconnectors (P207, Upchurch Scientific, USA) and fittings (F331, Upchurch Scientific, USA) for the Luer adapters (P659, Upchurch Scientific, USA), the MPB and a waste bottle. The silicone tubing is gas permeable and equilibriates in an incubator the medium with oxygen while perfusing.

Example 5

Immunocytochemistry

The hESC colonies were characterised by indirect immunochemistry. hESC colonies in control wells and MPB were fixed with 4% (v/v) paraformaldehyde (PDF) in phosphate buffered saline (PBS) for 20 minutes and washed three times in PBS supplemented with 10% (v/v) FBS to block non specific binding (FIG. 6, step 6).

Primary monoclonal antibodies Oct-4 (SC-5279, Santa Cruz, USA), Tra-1-81 (MAB4381, Chemicon, UK) and SSEA-3 (MAB4303, Chemicon, UK) were used at a dilution of 1:200 and incubated with the cells for one hour at 37° C. The cells were then washed three times with PBS and incubated with secondary antibodies with excitation wavelengths of 488 nm (A21212, Invitrogen, USA) and 555 nm (A21426, Invitrogen, USA) for an hour at room temperature. Finally, the cells were stained with DAPI (D1306, Invitrogen, Carlsbad, Calif., USA). DAPI at a dilution of 1:200 was incubated with cells at room temperature for 10 minutes. The MPB and one well dishes were then washed three times with PBS. [0153] In addition, double staining using Tra-1-81 and SSEA-3 antibodies on the same colony was performed.

Example 6

Imaging

For the perfusion experiments and the control wells, we used an inverted microscope (Nikon Eclipse TE2000-U, Nikon Corporation, Japan) with a colour microscope camera (Nikon DS-Fil, Nikon Corporation, Japan) for daily inspection and endpoint assays.

To enhance the immunostaining contrast, the inventors used Photoshop (Photoshop CS3, Adobe Inc., USA).

Results

It was found that the hESC in the MPB were healthy and showed no difference compared to the controls demonstrating that the MPB does not have any detrimental effect on the hESC in any way. This was demonstrated by the fact that the pluripotency of the hESC determined by morphology and immunostaining seemed equal or better than in the static control dish, i.e. the hESC had retained their pluripotency.

DISCUSSION

The above described chip-to-world device offers a robust method of linking a microfluidic chip with the "macro-world." The interface includes a loading port, which can easily and repeatedly be opened and closed. Open, the port permits direct access to a microfluidic chamber. Once closed, the port is leak-free and permits perfusion of said chamber. This sealable port permits easy and gentle seeding of cells and extra-cellular matrix (ECM) compounds into the microfluidic chamber, the perfusion of the cells and, subsequently, their easy and gentle uptake from said chamber. The port also enables the loading and removal of beads or polymer monoliths, for example for enzymatic assays.

Furthermore, the device includes robust and leak-free interconnects for the introduction and collection of solutes (media, drug compounds) into and from the microfluidic chip. The interconnects self-align and seal without the need of O-rings to polymeric microfluidic chips. The location of the interconnects can easily be reconfigured. This ease of reconfiguration enables the microfluidic chip to be specifically designed according to the particular application requirements and independently of chip-to-world design limitations, thereby facilitating rapid prototyping of complete microfluidic devices. Moreover, the device enables the complete encapsulation of a polymeric microfluidic chip in a multi-layer fashion. Again, the device can be opened and closed easily and repeatedly. This multi-layer encapsulation not only enhances the achievable degree of complexity for the microfluidic chip itself (and thus its degree of functionality), but also accepts standard glass microscope slides or polystyrene plates. The use of standard material then facilitates the comparison of microfluidic assays with traditional assays (for example the comparison of traditional cell culturing techniques with microfluidic cell culturing via using the same substrate material). The facile opening and closing of the encapsulation enables the insertion and removal of standard material and thereby simplifies pre- and post-processing steps, which may have to be conducted and transported to and from conventional larger-scale equipment. Finally, the interconnects could potentially be standardized for easy linkage with 'robotized' liquid handling platforms and all materials can be autoclaved, which further broadens the applicability of the device. The described device enables the realization of microfluidic cell culture systems suitable for drug discovery and drug toxicity testing with minute amounts of cells, tightly controllable environmental conditions, and ease of optical interrogation.

Having thus described, in detail, preferred embodiments of the present disclosure, it is to be understood that the invention defined by the above paragraphs is not to be limited to particular details set forth in the above description as many apparent variations thereof are possible without departing from the spirit or scope of the present disclosure.

REFERENCES

The following references are referred to above and are incorporated herein by reference:

1. A. Manz, N. Graber and H. M. Widmer, Sens. Actuators B, 1990, 1, 244-248.
2. D. R. Reyes, D. Iossifidis, P.-A. Auroux and A. Manz, Anal. Chem., 2002, 74, 2623-2636.
3. P. A. Auroux, D. Iossifidis, D. R. Reyes and A. Manz, Anal. Chem., 2002, 74, 2637-2652.
4. S. A. Soper, S. M. Ford, S. Qi, R. L. McCarley, K. Kelly and M. C. Murphy, Anal. Chem., 2000, 72, 642A-651A.
5. T. D. Boone, Z. H. Fan, H. H. Hooper, A. J. Ricco, H. Tan and S. J. Williams, Anal. Chem., 2002, 74, 78A-86A.
6. C. G. Koh, W. Tan, M. Zhao, A. J. Ricco and Z. H. Fan, Anal. Chem., 2003, 75, 4591-4598.
7. E. T. Lagally, C. A. Emrich and R. A. Mathies, Lab Chip, 2001, 1, 102-107.
8. M. A. Bums, B. N. Johnson, S. N. Brahmasandra, K. Handique, J. R. Webster, M. Krishnan, T. S. Sammarco, P. M. Man, D. Jones, D. Heldsinger, C. H. Mastrangelo and D. T. Burke, Science, 1998, 282, 484-487.
9. R. H. Liu, J. Yang, R. Lenigk, J. Bonanno and P. Grodzinski, Anal. Chem., 2004, 76, 1824-1831.
10. A. T. Woolley, D. Hadley, P. Landre, A. J. deMello, R. A. Mathies and M. A. Northrup, Anal. Chem., 1996, 23, 4081-4086.
11. Z. H. Fan, W. Tan, H. Tan, X. C. Qiu and T. D. Boone, Micro Total Analysis Systems, ed. J. M. Ramsey and A. van den Berg, Kluwer Academic Publishers, Netherlands, 2001, pp. 19-21.
12. C. F. Chou, O. Bakajin, S. W. P. Turner, T. A. J. Duke, S. S. Chan, E. C. Cox, H. G. Craighead and R. H. Austin, Proc. Natl. Acad. Sci. USA, 1999, 96, 13762-13765.
13. N. Goedecke, B. McKenna, S. El-Difrawy, L. Carey, P. Matsudaira and D. Ehrlich, Electrophoresis, 2004, 25, 1678-1686.
14. A. G. Hadd, D. E. Raymond, J. W. Halliwell, S. Jacobson and J. M. Ramsey, Anal. Chem., 1997, 69, 3407-3412.
15. G. H. Seang, J. Heo and R. M. Crooks, Anal. Chem., 2003, 75, 3161-3167.
16. D. S. Peterson, T. Rohr, F. Svec and J. M. J. Frechet, Anal. Chem., 2003, 75, 5328-5335.
17. A. E. Herr, J. I. Molho, K. A. Drouvalakis, J. C. Mikkelsen, P. J. Utz, J. G. Santiago and T. W. Kenny, Anal. Chem., 2003, 75, 1180-1187.
18. W. Tan, Z. H. Fan, C. X. Qiu, A. J. Ricco and I. Gibbons, Electrophoresis, 2002, 23, 3638-3645.
19. L. J. Jin, B. C. Giordano and J. P. Landers, Anal. Chem., 2001, 73, 4994-4999.
20. A. Dodge, K. Fluri, E. Verpoorte and N. F. de Rooij, Anal. Chem., 2001, 73, 3400-3409.
21. K. Sato, M. Tokeshi, T. Odake, H. Kimura, T. Ooi, M. Nakao and T. Kitamori, Anal. Chem., 2000, 72, 1144-1147.
22. N. Chiem and D. J. Harrison, Anal. Chem., 1997, 69, 373-378.
23. K. Sato, M. Yamanaka, H. Takahashi, M. Tokeshi, H. Kimura and T. Kitamori, Electrophoresis, 2002, 23, 734-739.
24. J. Moorthy, G. A. Mensing, D. Kim, S. Mohanty, T. Eddington, W. H. Tepp, E. A. Johnson and D. J. Beebe, Electrophoresis, 2004, 25, 1705-1713.
25. D. T. Chiu, N. L. Jeon, S. Huang, R. S. Kane, C. Wargo, I. S. Choi, D. E. Ingber and G. M. Whitesides, Proc. Natl. Acad. Sci. USA, 2000, 97, 2408-2413.
26. M. G. Roper, J. G. Shackman, G. M. Dahlgren and R. T. Kennedy, Anal. Chem., 2003, 75, 4711-4717.
27. E. Tamaki, K. Sato, M. Tokeshi, K. Sato, M. Aihara and T. Kitamori, Anal. Chem., 2002, 74, 1560-1564. [0247] 28. P. C. H. Li and D. J. Harrison, Anal. Chem., 1997, 69, 1564-1568.
29. E. A. Schilling, A. E. Kamholz and P. Yager, Anal. Chem., 2002, 74, 1798-1804.
30. G. lesson, G. Kylberg and P. Andersson, Micro Total Analysis System' 2003, ed. M. A. Nothrup, K. F. Jensen and D. J. Harrison, 2003, pp. 155-158.
31. V. Nittis, R. Fortt, C. H. Legge and A. J. de Mello, Lab Chip, 2001, 1, 128-152.
32. A. Puntambekar and C. H. Ahn, J. Micromech. Microeng., 2002, 12, 35-40.
33. C. Gonzalez, S. D. Collins and R. L. Smith, Sens. Actuators B, 1998, 49, 40-45.
34. H. Chen, D. Acharya, A. Gajraj and J.-C. Mei-ners, Anal. Chem., 2003, 75, 5287-5291.
35. J. M. Ramsey, Nat. Biotechnol., 1999, 17, 1061-1062.
36. S. Attiya, A. B. Jemere, T. Tang, G. Fitzpatrick, Seiler, N. Chiem and D. J. Harrison, Electrophoresis, 2001, 22, 318-327.
37. N. H. Bings, C. Wang, C. D. Skinner, C. L. Colyer, P. Thibault and D. J. Harrison, Anal. Chem., 1999, 71, 3292-3296.
38. Z. Yang and R. Maeda, Electrophoresis, 2002, 23, 3474-3478.
39. Jian Liu, Jian Carl Hansen and R. Quake Stephen, Anal. Chem., 2003, 75, 4718-4723.
40. Khademhosseini A, Langer R, Borenstein J, Vacanti J P. Proc. Natl. Acad. Sci. U.S.A. 2006 Feb. 21; 103(8):2480-7.
41. H. Andersson and A. van den Berg, Lab Chip 4, 98 (2004)

All documents, patents, journal articles and other materials cited in the present application are incorporated herein by reference.

While the present disclosure has been disclosed with references to certain embodiments, numerous modification, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

What is claimed is:

1. A method of using a microfluidic device comprising:

providing a microfluidic device comprising:

a chamber having a fluid inlet, and a fluid outlet and a sealable port, wherein the fluid inlet and the fluid outlet are positioned to direct fluid flowing from the fluid inlet to the fluid outlet through the chamber, and wherein the sealable port is aligned with the chamber to allow material to be placed directly into, or removed from, the chamber from the exterior of the device when the sealable port is open, and to prevent fluid escaping through the sealable port when the sealable port is sealed, and a lid configured to seal the sealable port in a sealed position when the lid fills part of a volume of the chamber in a closed position, wherein the chamber has a smaller volume in the sealed position, wherein the lid is configured to unseal the sealable port in an unsealed position when the lid is removed from the part of a volume of the chamber in an open position, wherein the chamber has a larger volume in the open position, wherein the lid is in contact with the side walls of the chamber when the sealable port is closed, wherein the device is operable when the sealable port is open or closed, and wherein the sealable port can be opened or closed during use of the device, wherein the fluid inlet and the fluid outlet comprise a plurality of flow restrictors that partially obstruct the fluid inlet and fluid outlet to form a plurality of equally sized channels which at least partially homogenize a flow velocity and shear stress profile across the chamber, wherein a first conduit carries fluid to the fluid inlet and the first conduit increases in cross sectional area as it approaches the fluid inlet, and a second conduit carries fluid away from the fluid outlet and the second conduit decreases in cross sectional area as it becomes more distant from the fluid outlet, wherein each of the first and second conduits comprises a plurality of flow dividers positioned in the portion of the conduit which is changing in cross sectional area, wherein the flow dividers are configured to increase a uniformity of the flow velocity;

culturing cells and/or performing cell-based or enzymatic assays; increasing the uniformity of flow velocity via the one or more flow dividers.

2. A method of treating cell cultures in a microfluidic device comprising:

providing a microfluidic device comprising:

a chamber having a fluid inlet, and a fluid outlet and a sealable port, wherein the fluid inlet and the fluid outlet are positioned to direct fluid flowing from the fluid inlet to the fluid outlet through the chamber, and wherein the sealable port is aligned with the chamber to allow material to be placed directly into, or removed from, the chamber from the exterior of the device when the sealable port is open, and to prevent fluid escaping through the sealable port when the sealable port is sealed, and a lid configured to seal the sealable port in a sealed position when the lid fills part of a volume of the chamber in a closed position, wherein the chamber has a smaller volume in the sealed position, wherein the lid is configured to unseal the sealable port in an unsealed position when the lid is removed from the part of a volume of the chamber in an open position, wherein the chamber has a larger volume in the open position, wherein the lid is in contact with the side walls of the chamber when the sealable port is closed, wherein the device is operable when the sealable port is open or closed, and wherein the sealable port can be opened or closed during use of the device, wherein the fluid inlet and the fluid outlet comprise a plurality of flow restrictors that partially obstruct the fluid inlet and fluid outlet to form a plurality of equally sized channels which at least partially homogenize a flow velocity and shear stress profile across the chamber, wherein a first conduit carries fluid to the fluid inlet and the first conduit increases in cross sectional area as it approaches the fluid inlet, and a second conduit carries fluid away from the fluid outlet and the second conduit decreases in cross sectional area as it becomes more distant from the fluid outlet, wherein each of the first and second conduits comprises a plurality of flow dividers positioned in the portion of the conduit which is changing in cross sectional area, wherein the flow dividers are configured to increase a uniformity of the flow velocity;

configuring the device to culture or produce cells;

culturing or producing the cells; configuring the device to perform cell-based or enzymatic assays within the same device; performing cell-based or enzymatic assays;

and increasing the uniformity of flow velocity via the one or more flow dividers.

3. A method of using a microfluidic device comprising:

providing a microfluidic device comprising:

a chamber having a fluid inlet, and a fluid outlet and a sealable port, wherein the fluid inlet and the fluid outlet are positioned to direct fluid flowing from the fluid inlet to the fluid outlet through the chamber, and wherein the sealable port is aligned with the chamber to allow material to be placed directly into, or removed from, the chamber from the exterior of the device when the sealable port is open, and to prevent fluid escaping through the sealable port when the sealable port is sealed, and a lid configured to seal the sealable port in a sealed position when the lid fills part of a volume of the chamber in a closed position, wherein the chamber has a smaller volume in the sealed position, wherein the lid is configured to unseal the sealable port in an unsealed position when the lid is removed from the part of a volume of the chamber in an open position, wherein the chamber has a larger volume in the open position, wherein the lid is in contact with the side walls of the chamber when the sealable port is closed, wherein the device is operable when the sealable port is open or closed, and wherein the sealable port can be opened or closed during use of the device, wherein the fluid inlet and the fluid outlet comprise a plurality of flow restrictors that partially obstruct the fluid inlet and fluid outlet to form a plurality of equally sized channels which at least partially homogenize a flow velocity and shear stress profile across the chamber, wherein a first conduit carries fluid to the fluid inlet and the first conduit increases in cross sectional area as it approaches the fluid inlet, and a second conduit carries fluid away from the fluid outlet and the second conduit decreases in cross sectional area as it becomes more distant from the fluid outlet, wherein each of the first and second conduits comprises a plurality of flow dividers positioned in the portion of the conduit which is changing in cross sectional area, wherein the flow dividers are configured to increase a uniformity of the flow velocity;

seeding cells in the device when the sealable port is open;

perfusing the cells when the sealable port is closed;

and increasing the uniformity of flow velocity via the one or more flow dividers.

4. A method of treating cells in a microfluidic device of comprising:

providing a microfluidic device comprising:

a chamber having a fluid inlet, and a fluid outlet and a sealable port, wherein the fluid inlet and the fluid outlet are positioned to direct fluid flowing from the fluid inlet to the fluid outlet through the chamber, and wherein the sealable port is aligned with the chamber to allow material to be placed directly into, or removed from, the chamber from the exterior of the device when the sealable port is open, and to prevent fluid escaping through the sealable port when the sealable port is sealed, and a lid configured to seal the sealable port in a sealed position when the lid fills part of a volume of the chamber in a closed position, wherein the chamber has a smaller volume in the sealed position, wherein the lid is configured to unseal the sealable port in an unsealed position when the lid is removed from the part of a volume of the chamber in an open position, wherein the chamber has a larger volume in the open position, wherein the lid is in contact with the side walls of the chamber when the sealable port is closed, wherein the device is operable when the sealable port is open or closed, and wherein the sealable port can be opened or closed during use of the device, wherein the fluid inlet and the fluid outlet comprise a plurality of flow restrictors that partially obstruct the fluid inlet and fluid outlet to form a plurality of equally sized channels which at least partially homogenize a flow velocity and shear stress profile across the chamber, wherein a first conduit carries fluid to the fluid inlet and the first conduit increases in cross sectional area as it approaches the fluid inlet, and a second conduit carries fluid away from the fluid outlet and the second conduit decreases in cross sectional area as it becomes more distant from the fluid outlet, wherein each of the first and second conduits comprises a plurality of flow dividers positioned in the portion of the conduit which is changing in cross sectional area, wherein the flow dividers are configured to increase a uniformity of the flow velocity;

configuring the device to seed or produce cells in the device;

seeding or producing the cells in the device; configuring the device to perfuse the cells in the same device;

perfusing the cells; and increasing the uniformity of flow velocity via the one or more flow dividers.

5. A method of performing cell seeding and microfluidics in a multifunctional dual mode microfluidic device comprising:

providing a microfluidic device comprising:

a chamber having a fluid inlet, and a fluid outlet and a sealable port, wherein the fluid inlet and the fluid outlet are positioned to direct fluid flowing from the fluid inlet to the fluid outlet through the chamber, and wherein the sealable port is aligned with the chamber to allow material to be placed directly into, or removed from, the chamber from the exterior of the device when the sealable port is open, and to prevent fluid escaping through the sealable port when the sealable port is sealed, and a lid configured to seal the sealable port in a sealed position when the lid fills part of a volume of the chamber in a closed position, wherein the chamber has a smaller volume in the sealed position, wherein the lid is configured to unseal the sealable port in an unsealed position when the lid is removed from the part of a volume of the chamber in an open position, wherein the chamber has a larger volume in the open position, wherein the lid is in contact with the side walls of the chamber when the sealable port is closed, wherein the device is operable when the sealable port is open or closed, and wherein the sealable port can be opened or closed during use of the device, wherein the fluid inlet and the fluid outlet comprise a plurality of flow restrictors that partially obstruct the fluid inlet and fluid outlet to form a plurality of equally sized channels which at least partially homogenize a flow velocity and shear stress profile across the chamber, wherein a first conduit carries fluid to the fluid inlet and the first conduit increases in cross sectional area as it approaches the fluid inlet, and a second conduit carries fluid away from the fluid outlet and the second conduit decreases in cross sectional area as it becomes more distant from the fluid outlet, wherein each of the first and second conduits comprises a plurality of flow dividers positioned in the portion of the conduit which is changing in cross sectional area, wherein the flow dividers are configured to increase a uniformity of the flow velocity;

configuring the device into a first operating configuration;

performing static cell seeding in the first operating configuration of the device;

configuring the device into a second operating configuration;

performing perfusion via microfluidics in the second operating configuration of the device, wherein the device is configured to switch between the first operating configuration and the second operating configuration;

and increasing the uniformity of flow velocity in the multifunctional dual mode microfluidic device.

6. The method of claim 5, wherein the first operating configuration and the second operating configuration are selectively accessible.

7. The method of claim 5, wherein the first operating configuration comprises an open chamber having a fluid inlet and a fluid outlet, wherein the fluid inlet and the fluid outlet are positioned to direct fluid flowing from the fluid inlet to the fluid outlet through the chamber, and wherein chamber is configured to allow material to be placed directly into, or removed from, the chamber from the exterior of the device.

8. The method of claim 7, wherein a sealable port is aligned with the chamber to allow material to be placed directly into, or removed from the chamber from the exterior of the device.

9. The method of claim 5, wherein the second operating configuration comprises a closed chamber having a fluid inlet and a fluid outlet and a sealable port, wherein the fluid inlet and the fluid outlet are positioned to direct fluid flowing from the fluid inlet to the fluid outlet through the chamber, and wherein the sealable port is aligned with the chamber to prevent fluid escaping through the sealable port when the sealable port is sealed, and a lid configured to seal the sealable port in a sealed position when the lid fills part of a volume of the chamber in a closed position, wherein the lid contact side walls of the chamber when the sealable port is closed.

10. The method of claim 9, wherein a volume of the chamber is adjusted based on changing a dimension of the lid.

11. The method of claim 9, wherein the lid forms an uppermost portion of the chamber.

12. The method of claim 9, wherein the lid is positioned at any location within the chamber.

13. The method of claim 9, wherein the lid comprises a deformable material.

14. The method of claim 9, wherein the lid comprises a gas permeable material.

15. The method of claim 9, wherein the lid comprises a protrusion, wherein the protrusion is configured to seal the sealable port in a sealed position such that the protrusion fills part of the volume of the chamber in the closed position, wherein the protrusion is configured to unseal the sealable port in the unsealed position such that the protrusion is removed from the part of the volume of the chamber in the open position.

16. The method of claim 15, wherein the protrusion of the lid contacts the side walls of the chamber when the sealable port is closed.

17. The method of claim 15, wherein a volume of the chamber is adjustable based on changing a dimension of the protrusion.

18. The method of claim 15, wherein the protrusion forms an uppermost portion of the chamber.

19. The method of claim 15, wherein the protrusion is disposed at any position within the chamber.

20. The method of claim 9, wherein a base of the chamber is formed from a substrate for supporting biological material, and the chamber is formed on at least a portion of the substrate.

21. A method of using a microfluidic device comprising:

providing a microfluidic device comprising:

a chamber having a fluid inlet, and a fluid outlet; a sealable port, wherein the fluid inlet and the fluid outlet are positioned to direct fluid flowing from the fluid inlet to the fluid outlet through the chamber, and wherein the sealable port is aligned with the chamber to allow material to be placed directly into, or removed from, the chamber from the exterior of the device when the sealable port is open, and to prevent fluid escaping through the sealable port when the sealable port is sealed, wherein the chamber is formed on a first layer of the device, wherein a base of the chamber is formed from a substrate for supporting biological material, and the chamber is formed on at least a portion of the substrate, wherein the substrate is formed on another layer of the device; and a lid configured to seal the sealable port in a sealed position when the lid fills part of a volume of the chamber in a closed position, wherein the chamber has a smaller volume in the sealed position, wherein the lid is configured to unseal the sealable port in an unsealed position when the lid is removed from the part of a volume of the chamber in an open position, wherein the chamber has a larger volume in the open position, wherein the lid is in contact with the side walls of the chamber when the sealable port is closed, wherein the device is operable when the sealable port is open or closed, and wherein the sealable port can be opened or closed during use of the device, wherein the fluid inlet and the fluid outlet comprise a plurality of flow restrictors that partially obstruct the fluid inlet and fluid outlet to form a plurality of equally sized channels which at least partially homogenize a flow velocity and shear stress profile across the chamber, wherein a first conduit carries fluid to the fluid inlet and the first conduit increases in cross sectional area as it approaches the fluid inlet, and a second conduit carries fluid away from the fluid outlet and the second conduit decreases in cross sectional area as it becomes more distant from the fluid outlet, wherein each of the first and second conduits comprises a plurality of flow dividers positioned in the portion of the conduit which is changing in cross sectional area, wherein the flow dividers are configured to increase a uniformity of the flow velocity;

culturing or producing cells and/or performing cell-based or enzymatic assays;

and increasing the uniformity of flow velocity via the one or more flow dividers.

* * * * *